(12) United States Patent
Kobayashi et al.

(10) Patent No.: US 9,309,532 B2
(45) Date of Patent: Apr. 12, 2016

(54) IRON-ZINC BINDING CONTROL FACTOR, AND TECHNIQUE FOR IMPROVING IRON DEFICIENCY TOLERANCE OF PLANT AND ENHANCING IRON AND ZINC ACCUMULATION IN EDIBLE PART THEREOF BY CONTROLLING EXPRESSION OF NOVEL IRON-ZINC BINDING CONTROL FACTOR

(71) Applicant: Japan Science and Technology Agency, Kawaguchi-shi, Saitama (JP)

(72) Inventors: Takanori Kobayashi, Nonoichi (JP); Naoko Nishizawa, Nonoichi (JP)

(73) Assignee: JAPAN SCIENCE AND TECHNOLOGY AGENCY, Kawaguchi-Shi (JP)

( * ) Notice: Subject to any disclaimer, the term of this patent is extended or adjusted under 35 U.S.C. 154(b) by 0 days.

(21) Appl. No.: 14/390,498

(22) PCT Filed: Jul. 19, 2013

(86) PCT No.: PCT/JP2013/069628
§ 371 (c)(1),
(2) Date: Oct. 3, 2014

(87) PCT Pub. No.: WO2014/017394
PCT Pub. Date: Jan. 30, 2014

(65) Prior Publication Data
US 2015/0299722 A1    Oct. 22, 2015

(30) Foreign Application Priority Data

Jul. 26, 2012 (JP) ................................. 2012-166233

(51) Int. Cl.
*C12N 15/82* (2006.01)
*C07K 16/16* (2006.01)
*C07K 14/415* (2006.01)

(52) U.S. Cl.
CPC .......... *C12N 15/8261* (2013.01); *C07K 14/415* (2013.01); *C07K 16/16* (2013.01); *C12N 15/8218* (2013.01); *C12N 15/8243* (2013.01); *C12N 15/8257* (2013.01); *C12N 15/8271* (2013.01)

(58) Field of Classification Search
None
See application file for complete search history.

(56) References Cited

U.S. PATENT DOCUMENTS

2004/0123343 A1* 6/2004 La Rosa et al. ............. 800/278
2006/0123505 A1* 6/2006 Kikuchi et al. ............. 800/278
2011/0138496 A1* 6/2011 Nishizawa et al. .......... 800/278

FOREIGN PATENT DOCUMENTS

JP 2005-185101 A 7/2005
WO WO 2010/100595 A2 * 9/2010

OTHER PUBLICATIONS

Kobayashi et al., 2013, Nature Communications 4: 1-12, doi:10.1038/ncomms3792.*
Ogo et al., 2006, Journal of Experimental Botany 57: 2867-2878.*
Keskin et al., 2004, Protein Science 13: 1043-1055.*
Guo et al., 2004, Proceedings of the National Academy of Sciences USA 101: 9205-9210.*
Thornton et al., 2000, Nature Structural Biology, structural genomic supplement, Nov. 2000: 991-994.*
Maniatis et al., 1982, Molecular Cloning: A Laboratory Manual, Cold Spring Harbor Laboratory, see, in particular, pp. 324-343 and 387-389.*
Small, 2007, Current Opinion in Biotechnology 18: 148-153.*
Roth et al., 2004, Virus Research 102: 97-108.*
Schultes and Bartel, 2000, Science 289: 448-452.*
Gelvin, 2003, Microbiology and Molecular Biology Reviews 67: 16-37.*
Kobayashi and Nishizawa, 2012, Annu. Rev. Plant Biol. 63: 131-152.*
Sasaki, T. et al., "Zinc finger protein-like [Oryza sativa Japonica Group]", GenBank Accession No. BAD82554.1, [online] <http://www.ncbi.nlm.nih.gov/protein/56784461?report=genbank>, retrieved Mar. 26, 2015.
State Intellectual Property Office of People's Republic of China, "Office Action", received for Chinese Patent Application No. 201380018432.9, issued on Apr. 8, 2015, 14 pages (8 pages of English Translation of Office Action, 6 pages of Office Action).
M. Chow et al., "Synthetic peptides from four separate regions of the poliovirus type 1 capsid protein VP1 induce neutralizing antibodies," Proc. Natl. Acad. Sci. USA, vol. 82, pp. 910-914, Feb. 1985.

(Continued)

*Primary Examiner* — Amjad Abraham
*Assistant Examiner* — Bratislav Stankovic

(57) ABSTRACT

According to the present invention, a transformant and a gene-disrupted strain are provided which exhibit growth superior to that of ordinary plants in calcareous soil, and which can accumulate iron and zinc in large quantities in both calcareous soil and good soil; also provided are a gene, vector, protein, and antibody used for constructing these, and a method of construction, a composition for construction, a kit for construction, and a breeding method for a plant with improved iron deficiency tolerance, and enhanced iron and zinc accumulation in an edible part. The protein of the present invention is an iron- and zinc-binding regulatory factor, and includes any one of the following amino acid sequences of (a) to (c): (a) an amino acid sequence represented by SEQ ID NO:1 or 2; (b) an amino acid sequence obtained by deletion, substitution, or addition of one to several amino acids in the amino acid sequence represented by SEQ ID NO:1 or 2; or (c) an amino acid sequence which has 80% or more identity with the amino acid sequence represented by SEQ ID NO:1 or 2.

4 Claims, 21 Drawing Sheets

(56) References Cited

OTHER PUBLICATIONS

Yu, J. et al., "Definition: Oryza sativa (indica cultivar-group) chromosome 1, whole genome shotgun sequence," Database GenBank [online], Accession No. CM000126 Region: 31695449 . . . 31706033, <http://www.ncbi.nlm.nih.gov/nuccore/CM000126>, Dec. 17, 2008.
Fumiyuki Goto et al., "Iron fortification of rice seed by the soybean ferritin gene," Nature Biotechnology, vol. 17, pp. 282-286, Mar. 1999.
Yukoh Hiei et al., "Efficient transformation of rice (*Oryza sativa* L) mediated by Agrobacterium and sequence analysis of the boundaries of the T-DNA," The Plant Journal, vol. 6 (2), pp. 271-282, 1994.
Yasuhiro Ishimaru et al., "Mutational reconstructed ferric chelate reductase confers enhanced tolerance in rice to iron deficiency in calcareous soil," Proceedings of the National Academy of Sciences, vol. 104, No. 18, pp. 7373-7378, May 1, 2007.
Yasuhiro Ishimaru et al., "Rice metal-nicotianamine transporter, OsYSL2, is required for the long-distance transport of iron and manganese," The Plant Journal, vol. 62, pp. 379-390, 2010.
Japan Patent Office, "International Search Report," issued in PCT/JP2013/069628, mailed on Sep. 24, 2013.
Takanori Kobayashi et al., "In vivo evidence that Ids3 from Hordeum vulgare encodes a dioxygenase that converts 2'-deoxymugineic acid to mugineic acid in transgenic rice," Planta, vol. 212, pp. 864-871, 2001.
Takanori Kobayashi et al., "Plant Iron Deficiency Reaction Mechanism," Hematology Frontier, vol. 22, No. 1, pp. 100-104, Dec. 30, 2011.
G. Köhler et al., "Continuous cultures of fused cells secreting antibody of predefined specificity," Nature, vol. 256, pp. 495-497, Aug. 7, 1975.
Sichul Lee et al., "Iron fortification of rice seeds through activation of the nicotianamine synthase gene," Proceedings of the National Academy of Sciences, vol. 106, No. 51, pp. 22014-22019, Dec. 22, 2009.
Hiroshi Masuda et al., "Increase in Iron and Zinc Concentrations in Rice Grains Via the Introduction of Barley Genes Involved in Phytosiderophore Synthesis," Rice, vol. 1, pp. 100-108, 2008.
Hiroshi Masuda et al., "Overexpression of the Barley Nicotianamine Synthase Gene HvNAS1 Increases Iron and Zinc Concentrations in Rice Grains," Rice, vol. 2, pp. 155-166, 2009.
Judith Wirth et al., "Rice endosperm iron biofortification by targeted and synergistic action of nicotianamine synthase and ferritin," Plant Biotechnology Journal, vol. 7, pp. 1-14, Sep. 2009.
Yuko Ogo et al., "OsIRO2 is responsible for iron utilization in rice and improves growth and yield in calcareous soil," Plant Molecular Biology, 75, pp. 593-605, 2011.
Yuko Ogo et al., "Isolation and characterization of IRO2, a novel iron-regulated bHLH transcription factor in graminaceous plants," Journal of Experimental Botany, vol. 57, No. 11, pp. 2867-2878, 2006.
Yuko Ogo et al., "The rice bHLH protein OsIRO2 is an essential regulator of the genes involved in Fe uptake under Fe-deficient conditions," The Plant Journal, vol. 51, pp. 366-377, 2007.
Kenjirou Ozawa et al., "Development of an Efficient Agrobacterium-Mediated Gene Targeting System for Rice and Analysis of Rice Knockouts Lacking Granule-Bound Starch Synthase (Waxy) and b1,2-Xylosyltransferase," Plant & Cell Physiology, vol. 53, Issue 4, pp. 755-761, 2012.
Tracey A. Rouault, "An Ancient Gauge for Iron," Science, vol. 326, pp. 676-677, Oct. 30, 2009.
Ameen A. Salahudeen et al., "An E3 ligase possessing an iron-responsive hemerythrin domain is a regulator of iron homeostasis," Science, vol. 326, pp. 722-726, Oct. 30, 2009.
Motofumi Suzuki et al., "Transgenic rice lines that include barley genes have increased tolerance to low iron availability in a calcareous paddy soil," Soil Science and Plant Nutrition, vol. 54, pp. 77-85, 2008.
Michiko Takahashi et al., "Enhanced tolerance of rice to low iron availability in alkaline soils using barley nicotianamine aminotransferase genes," Nature Biotechnology, vol. 19, pp. 466-469, May 2001.
Rie Terada et al., "Gene Targeting by Homologous Recombination as a Biotechnological Tool for Rice Functional Genomics," Plant Physiology, vol. 144, pp. 846-856, Jun. 2007.
Cristobal Uauy et al., "A NAC Gene Regulating Senescence Improves Grain Protein, Zinc, and Iron Content in Wheat," Science, vol. 314, pp. 1298-1301, Nov. 24, 2006.
Ajay A. Vashisht et al., "Control of Iron Homeostasis by an Iron-Regulated Ubiquitin Ligase," Science, vol. 326, pp. 718-721, Oct. 30, 2009.

* cited by examiner

☒ :Hemerythrin/HHE cation-binding motif
☒ :CHY-type zinc-finger domain
■ :CTCHY-type zinc-finger domain
☐ :RING zinc-finger domain
☒ :Rubredoxin-type fold FIG. 4
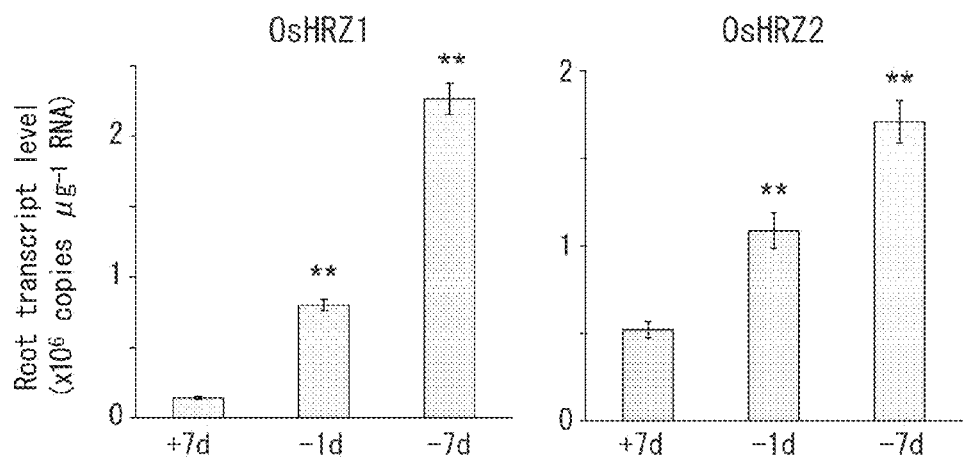
(a)
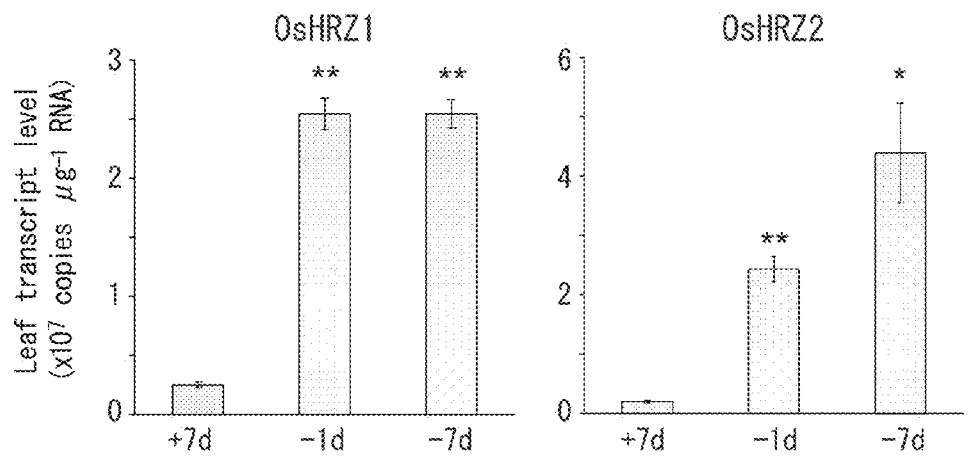
(b)

FIG. 20
(a)
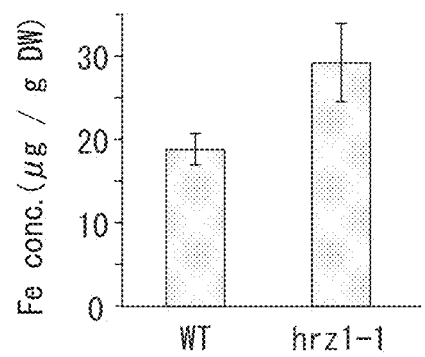
(b)
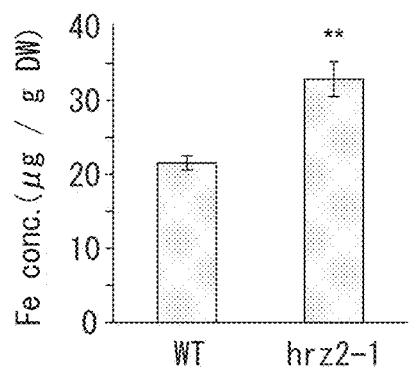

FIG. 21
(a)
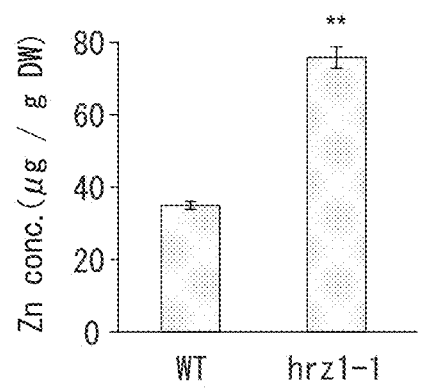
(b)
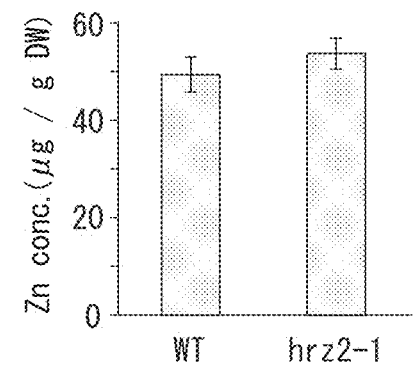

FIG. 24

| RAP Locus | Product name | +Fe 7d Root | | | -Fe 1d Root | | | -Fe 7d Root | | |
|---|---|---|---|---|---|---|---|---|---|---|
| | | 2i-1/NT | 2i-2/NT | 2i-3/NT | 2i-1/NT | 2i-2/NT | 2i-3/NT | 2i-1/NT | 2i-2/NT | 2i-3/NT |
| Hemerythrin domain-containing proteins | | | | | | | | | | |
| Os01g0689300 | HRZ1 | 0.96 | 0.95 | 0.98 | 1.00 | 0.91 | 0.87 | 0.63 | 0.67 | 0.72 |
| Os05g0551000 | HRZ2 | 0.60 | 0.70 | 0.55 | 0.68 | 0.72 | 0.56 | 0.51 | 0.65 | 0.42 |
| Os01g0861700 | HORZ1 | 0.83 | 0.98 | 0.85 | 1.15 | 1.03 | 1.02 | 0.80 | 0.79 | 1.05 |
| Gene regulation under Fe deficiency | | | | | | | | | | |
| Os01g0952800 | OsIRO2 | 4.52 | 2.42 | 6.45 | 2.58 | 1.22 | 2.65 | 0.74 | 0.59 | 1.20 |
| Os03g0379300 | OsIRO3 | 3.03 | 1.74 | 4.88 | 1.32 | 1.38 | 2.21 | 0.76 | 0.80 | 1.52 |
| Biosynthesis of MAs | | | | | | | | | | |
| Os03g0307300 | OsNAS1 | 27.49 | 55.61 | 70.76 | 16.03 | 3.36 | 5.99 | 1.03 | 0.85 | 0.98 |
| Os03g0307200 | OsNAS2 | 27.36 | 50.97 | 63.34 | 16.99 | 3.93 | 7.26 | 1.04 | 0.96 | 1.16 |
| Os07g0689600 | OsNAS3 | 3.29 | 3.63 | 4.54 | 1.22 | 4.10 | 3.02 | 3.91 | 7.00 | 8.39 |
| Os02g0306400 | OsNAAT1 | 4.59 | 7.32 | 9.33 | 2.59 | 1.64 | 2.80 | 1.08 | 0.71 | 1.16 |
| Os03g0237100 | OsDMAS1 | 8.10 | 8.92 | 8.31 | 1.88 | 1.02 | 1.37 | 1.11 | 0.64 | 1.14 |
| Fe uptake and/or translocation | | | | | | | | | | |
| Os11g0134900 | TOM1 | 4.77 | 11.84 | 22.56 | 1.98 | 3.56 | 4.48 | 0.99 | 0.82 | 1.26 |
| Os02g0650300 | OsYSL15 | 10.53 | 15.49 | 18.58 | 39.10 | 4.21 | 4.66 | 0.90 | 1.06 | 1.11 |
| Os11g0151500 | ENA1 | 6.40 | 7.13 | 5.88 | 4.25 | 1.33 | 2.04 | 1.21 | 0.88 | 1.58 |
| Os02g0649900 | OsYSL2 | 51.42 | 0.96 | 74.36 | 14.85 | 1.09 | 60.00 | 160.29 | 1.26 | 194.37 |
| Os03g0667500 | OsIRT1 | 1.82 | 3.28 | 3.32 | 2.39 | 1.41 | 1.61 | 0.72 | 0.81 | 1.13 |
| Os03g0667300 | OsIRT2 | 4.71 | 6.10 | 7.29 | 1.19 | 1.84 | 1.93 | 0.74 | 0.60 | 1.04 |
| Os07g0258400 | OsNRAMP1 | 5.51 | 3.72 | 6.63 | 1.79 | 1.60 | 2.19 | 0.90 | 0.75 | 1.21 |
| Fe storage | | | | | | | | | | |
| Os11g0106700 | OsFer1 | 0.60 | 0.47 | 0.46 | 0.85 | 0.84 | 0.72 | 1.13 | 0.93 | 0.98 |
| Os12g0106000 | OsFer2 | 0.58 | 0.49 | 0.47 | 0.80 | 0.83 | 0.71 | 0.99 | 0.89 | 0.89 |

SEQUENCE LISTING

```
<160> NUMBER OF SEQ ID NOS: 5

<210> SEQ ID NO 1
<211> LENGTH: 1236
<212> TYPE: PRT
<213> ORGANISM: Oryza sativa

<400> SEQUENCE: 1

Met Ala Thr Pro Thr Pro Met Ala Gly Glu Gly Thr Leu Ala Ala Val
 1               5                   10                  15

Met Pro Arg Ser Pro Ser Pro Thr Ala Ser Ala Ala Ala Gly Ser Ala
            20                  25                  30

Ala Glu Ala Pro Met Leu Ile Phe Leu Tyr Phe His Lys Ala Ile Arg
        35                  40                  45
```

```
            Ala Glu Leu Glu Gly Leu His Ala Ala Val Arg Leu Ala Thr Glu
             50                  55                  60

Arg Ala Gly Asp Val Gly Ala Leu Ala Glu Arg Cys Arg Phe Phe Val
         65                  70                  75                  80

Asn Ile Tyr Lys His His Cys Asp Ala Glu Asp Ala Val Ile Phe Pro
                         85                  90                  95

Ala Leu Asp Ile Arg Val Lys Asn Val Ala Gly Thr Tyr Ser Leu Glu
                    100                 105                 110

His Lys Gly Glu Asn Asp Leu Phe Ser Gln Leu Phe Ala Leu Leu Gln
                    115                 120                 125

Leu Asp Ile Gln Asn Asp Asp Ser Leu Arg Arg Glu Leu Ala Ser Cys
            130                 135                 140

Thr Gly Ala Ile Gln Thr Cys Leu Ser Gln His Met Ser Lys Glu Glu
        145                 150                 155                 160

Glu Gln Val Phe Pro Leu Leu Thr Lys Lys Phe Ser Tyr Glu Glu Gln
                            165                 170                 175

Ala Asp Leu Val Trp Gln Phe Leu Cys Asn Ile Pro Val Asn Met Met
                    180                 185                 190

Ala Glu Phe Leu Pro Trp Leu Ser Ser Val Ser Ser Asp Glu His
                    195                 200                 205

Glu Asp Ile Arg Ser Cys Leu Cys Lys Ile Val Pro Glu Glu Lys Leu
            210                 215                 220

Leu Gln Gln Val Val Phe Ala Trp Ile Glu Gly Lys Thr Thr Arg Lys
        225                 230                 235                 240

Val Thr Glu Asn Ser Thr Lys Ser Asn Ser Glu Ala Thr Cys Asp Cys
                            245                 250                 255

Lys Asp Ala Ser Ser Ile Asp His Ala Asp Asn His Ile Ser Ser His
                    260                 265                 270

Glu Asp Ser Lys Ala Gly Asn Lys Lys Tyr Ala Glu Ser Ile Asp Gly
                    275                 280                 285

Gln Val Glu Arg His Pro Ile Asp Glu Ile Leu Tyr Trp His Asn Ala
            290                 295                 300

Ile Arg Lys Glu Leu Ile Asp Ile Ala Glu Glu Thr Arg Arg Met Gln
        305                 310                 315                 320

Gln Ser Gly Asn Phe Ser Asp Ile Ser Ser Phe Asn Ala Arg Leu Gln
                            325                 330                 335

Phe Ile Ala Asp Val Cys Ile Phe His Ser Ile Ala Glu Asp Gln Val
                    340                 345                 350

Val Phe Pro Ala Val Asp Ser Glu Leu Ser Phe Val His Glu His Ala
                    355                 360                 365

Glu Glu Glu Arg Arg Phe Asn Asn Phe Arg Cys Leu Ile Gln Gln Ile
                    370                 375                 380

Gln Ile Ala Gly Ala Lys Ser Thr Ala Leu Asp Phe Tyr Ser Glu Leu
        385                 390                 395                 400

Cys Ser His Ala Asp Gln Ile Met Glu Thr Ile Glu Lys His Phe Cys
                            405                 410                 415

Asp Glu Glu Thr Lys Val Leu Pro Gln Ala Arg Met Leu Phe Ser Pro
                    420                 425                 430

Glu Lys Gln Arg Gln Leu Leu Tyr Lys Ser Leu Cys Val Met Pro Leu
                    435                 440                 445

Lys Leu Leu Glu Arg Val Leu Pro Trp Leu Val Ser Lys Leu Ser Asp
            450                 455                 460
```

```
Glu Glu Ala Ser Ser Phe Leu Glu Asn Met Arg Leu Ala Ala Pro Ser
465                 470                 475                 480

Ser Glu Thr Ala Leu Val Thr Leu Phe Ser Gly Trp Ala Cys Lys Ala
                485                 490                 495

Arg Ser Glu Asp Lys Ser Asn Ser Gly Glu Tyr Leu Cys Leu Thr Ser
            500                 505                 510

Gly Glu Met Arg Cys Leu Leu Asp Glu Val Asp Gly Leu Glu Lys Cys
        515                 520                 525

Arg Pro Phe Cys Pro Cys Ala Ser Arg Ser Asn Thr Asp Ala Ser Leu
    530                 535                 540

His Pro Gln Thr Glu Asn Gly Ser Arg Pro Gly Lys Arg Gly Asn Asp
545                 550                 555                 560

Ala Glu Ser Val Pro Gly Thr Asn Gly Ser Asp Leu Ser Gln Thr Asp
                565                 570                 575

Asp Thr Glu Ala Arg Pro Cys Ser Lys Lys Pro Cys Cys Ile Pro Gly
            580                 585                 590

Leu Arg Val Glu Thr Gly Asn Leu Ala Ile Ser Ser Leu Ala Ser
        595                 600                 605

Ala Lys Ser Phe Arg Ser Leu Ser Tyr Asn Ser Ser Ala Pro Ser Leu
    610                 615                 620

Tyr Ser Ser Leu Phe Ser Trp Glu Thr Asp Ala Ser Leu Ser Cys Ser
625                 630                 635                 640

Asp Gly Ile Ser Arg Pro Ile Asp Thr Ile Phe Lys Phe His Lys Ala
                645                 650                 655

Ile Arg Lys Asp Leu Glu Tyr Leu Asp Val Glu Ser Gly Lys Leu Ile
            660                 665                 670

Asp Gly Asp Glu Ser Cys Leu Arg Gln Phe Ile Gly Arg Phe Arg Leu
        675                 680                 685

Leu Trp Gly Leu Tyr Arg Ala His Ser Asn Ala Glu Asp Glu Ile Val
    690                 695                 700

Phe Pro Ala Leu Glu Ser Arg Gly Thr Leu His Asn Val Ser His Ser
705                 710                 715                 720

Tyr Thr Leu Asp His Lys Gln Glu Glu Gln Leu Phe Gly Asp Ile Ser
                725                 730                 735

Asp Ala Leu Ala Glu Leu Ser Gln Leu His Glu Arg Leu Thr His Pro
            740                 745                 750

His Ile Glu Val Ser Glu Ala Glu Lys Asn Asp Phe Asn Ser Ser Asp
        755                 760                 765

Glu Ile Asp Trp Thr Arg Lys Tyr Asn Glu Leu Ala Thr Lys Leu Gln
    770                 775                 780

Gly Met Cys Lys Ser Ile Arg Ala Ala Leu Thr Asn His Val His Arg
785                 790                 795                 800

Glu Glu Leu Glu Leu Trp Pro Leu Phe Asp Glu His Phe Ser Val Glu
                805                 810                 815

Glu Gln Asp Lys Leu Val Gly Arg Ile Ile Gly Ser Thr Gly Ala Glu
            820                 825                 830

Val Leu Gln Ser Met Leu Pro Trp Val Thr Ser Ala Leu Thr Gln Glu
        835                 840                 845

Glu Gln Asn Met Met Leu Asp Thr Trp Lys Gln Ala Thr Lys Asn Thr
    850                 855                 860

Met Phe Gly Glu Trp Leu Asn Glu Trp Trp Lys Gly Ala Pro Thr Ser
865                 870                 875                 880

Ser Asp Ser Ser Glu Glu Ala Ser Ser Ala Pro Glu Asp Ser His Leu
```

```
                        885                 890                 895
Gln Asp Lys Ile Asp Gln Asn Asp Gln Met Phe Lys Pro Gly Trp Lys
                    900                 905                 910
Asp Ile Phe Arg Met Asn Gln Ser Glu Leu Glu Ala Glu Val Arg Lys
                915                 920                 925
Val Ser Arg Asp Pro Thr Leu Asp Pro Arg Arg Lys Ala Tyr Leu Ile
            930                 935                 940
Gln Asn Leu Met Thr Ser Arg Trp Ile Ala Gln Gln Lys Leu Pro
945                 950                 955                 960
Glu Pro Lys Ser Glu Glu Cys Ser Gly Ala Gly Ile Pro Gly Cys
                965                 970                 975
Ala Pro Ser Tyr Arg Asp Gln Glu Lys Gln Ile Phe Gly Cys Glu His
                980                 985                 990
Tyr Lys Arg Asn Cys Lys Leu Val Ala Ala Cys Cys Asn Lys Leu Phe
                995                 1000                1005
Thr Cys Arg Phe Cys His Asp Lys Ile Ser Asp His Thr Met Glu Arg
            1010                1015                1020
Lys Ala Thr Gln Glu Met Met Cys Met Val Cys Leu Lys Val Gln Pro
1025                1030                1035                1040
Val Gly Pro Asn Cys Gln Thr Pro Ser Cys Asn Gly Leu Ser Met Ala
                1045                1050                1055
Lys Tyr Tyr Cys Asn Ile Cys Lys Phe Phe Asp Asp Glu Arg Thr Val
                1060                1065                1070
Tyr His Cys Pro Phe Cys Asn Leu Cys Arg Leu Gly Lys Gly Leu Gly
                1075                1080                1085
Val Asp Phe Phe His Cys Met Lys Cys Asn Cys Cys Leu Gly Met Lys
                1090                1095                1100
Leu Thr Glu His Lys Cys Arg Glu Lys Gly Leu Glu Thr Asn Cys Pro
1105                1110                1115                1120
Ile Cys Cys Asp Phe Leu Phe Thr Ser Ser Ala Ala Val Arg Ala Leu
                1125                1130                1135
Pro Cys Gly His Phe Met His Ser Ala Cys Phe Gln Ala Tyr Thr Cys
                1140                1145                1150
Ser His Tyr Thr Cys Pro Ile Cys Cys Lys Ser Leu Gly Asp Met Ala
                1155                1160                1165
Val Tyr Phe Gly Met Leu Asp Ala Leu Leu Ala Ala Glu Glu Leu Pro
                1170                1175                1180
Glu Glu Tyr Arg Asp Arg Cys Gln Asp Ile Leu Cys Asn Asp Cys Glu
1185                1190                1195                1200
Arg Lys Gly Arg Ser Arg Phe His Trp Leu Tyr His Lys Cys Gly Ser
                1205                1210                1215
Cys Gly Ser Tyr Asn Thr Arg Val Ile Lys Thr Asp Thr Ala Asp Cys
                1220                1225                1230
Ser Thr Pro Asn
        1235

<210> SEQ ID NO 2
<211> LENGTH: 811
<212> TYPE: PRT
<213> ORGANISM: Oryza sativa

<400> SEQUENCE: 2

Met Glu Lys Ile Glu Arg His Phe Lys Asn Glu Glu Thr Lys Val Leu
1               5                   10                  15
```

```
Pro Gln Ala Arg Ile His Phe Ser Ser Glu Lys Gln Arg Glu Leu Leu
             20                  25                  30

Tyr Lys Ser Leu Cys Val Ile Pro Leu Lys Leu Leu Glu Arg Val Leu
         35                  40                  45

Pro Trp Phe Val Ser Lys Leu Asn Asp Gln Asp Ala Glu Ala Phe Leu
     50                  55                  60

Gln Asn Met Phe Leu Ala Ala Pro Ser Ser Glu Ala Ala Leu Val Thr
 65                  70                  75                  80

Leu Leu Ser Gly Trp Ala Cys Lys Gly Arg Ser Lys Gly Thr Ser Asn
                 85                  90                  95

Ser Gly Lys Phe Ile Cys Leu Thr Pro Arg Ala Leu Ser Ser Pro Leu
            100                 105                 110

Asp Glu Asn Gly Phe Lys Asp Cys Gln Leu Cys Pro Cys Ser Leu Gln
        115                 120                 125

Ser Asp Ile Cys Ser Arg Pro Ala Lys Lys Trp Asn Asp Thr Glu Ser
130                 135                 140

Ser Asn Ile Ser Asn Cys Ser Gln Thr Ala Asp Ile Ala Leu Thr Cys
145                 150                 155                 160

Lys Asn Arg Pro Cys His Ile Pro Gly Leu Arg Val Glu Ile Ser Asn
                165                 170                 175

Leu Ala Val Asn Ser Phe Ala Ser Ala Glu Ser Phe Arg Ser Leu Ser
            180                 185                 190

Leu Asn Tyr Ser Ala Pro Ser Leu Tyr Ser Ser Leu Phe Ser Trp Glu
            195                 200                 205

Thr Asp Ala Ala Phe Ser Gly Pro Asp Asn Ile Ser Arg Pro Ile Asp
    210                 215                 220

Thr Ile Phe Lys Phe His Lys Ala Ile Arg Lys Asp Leu Glu Phe Leu
225                 230                 235                 240

Asp Val Glu Ser Arg Lys Leu Ile Asp Gly Asp Ser Ser Leu Arg
                245                 250                 255

Gln Phe Ile Gly Arg Phe Arg Leu Leu Trp Gly Leu Tyr Arg Ala His
                260                 265                 270

Ser Asn Ala Glu Asp Glu Ile Val Phe Pro Ala Leu Glu Ser Lys Glu
            275                 280                 285

Thr Leu His Asn Val Ser His Ser Tyr Thr Leu Asp His Lys Gln Glu
    290                 295                 300

Glu Glu Leu Phe Lys Asp Ile Ser Thr Ile Leu Phe Glu Leu Ser Gln
305                 310                 315                 320

Leu His Ala Asp Leu Lys His Pro Leu Gly Gly Ala Asp Ala Val Gly
                325                 330                 335

Ala Asn His Ile His Pro Tyr Asn Arg Ile Asp Trp Ser Lys Lys Asn
            340                 345                 350

Asn Glu Leu Leu Thr Lys Leu Gln Gly Met Cys Lys Ser Ile Arg Val
        355                 360                 365

Thr Leu Ser Asn His Val His Arg Glu Glu Leu Glu Leu Trp Pro Leu
    370                 375                 380

Phe Asp Lys His Phe Ser Val Glu Glu Gln Asp Lys Ile Val Gly Arg
385                 390                 395                 400

Ile Ile Gly Ser Thr Gly Ala Glu Val Leu Gln Ser Met Leu Pro Trp
                405                 410                 415

Val Thr Ser Ala Leu Ser Leu Asp Glu Gln Asn Asn Met Leu Asp Thr
            420                 425                 430

Trp Arg Gln Val Thr Lys Asn Thr Met Phe Asp Glu Trp Leu Asn Glu
```

```
                435                 440                 445
Trp Trp Lys Arg Ser Pro Thr Ser Ser Gly Pro Ser Ser Asp Ala Ser
450                 455                 460

His Pro Glu Glu Asp His Phe Gln Glu Lys Phe Asp Gln Ser Glu Gln
465                 470                 475                 480

Met Phe Lys Pro Gly Trp Lys Asp Ile Phe Arg Met Asn Gln Ser Glu
                485                 490                 495

Leu Glu Ala Glu Ile Arg Lys Val Ser Arg Asp Ser Thr Leu Asp Pro
            500                 505                 510

Arg Arg Lys Ala Tyr Leu Ile Gln Asn Leu Met Thr Ser Arg Trp Ile
        515                 520                 525

Ala Ala Gln Gln Lys Ser Pro Gln Pro Gln Ser Glu Asp Arg Asn Gly
    530                 535                 540

Cys Thr Val Leu Pro Gly Cys Cys Pro Ser Tyr Arg Asp Pro Glu Asn
545                 550                 555                 560

Gln Ile Phe Gly Cys Glu His Tyr Lys Arg Lys Cys Lys Leu Val Ala
                565                 570                 575

Ala Cys Cys Asn Lys Leu Phe Thr Cys Arg Phe Cys His Asp Lys Val
            580                 585                 590

Ser Asp His Thr Met Glu Arg Lys Ala Thr Val Glu Met Met Cys Met
        595                 600                 605

Gln Cys Leu Lys Val Gln Pro Val Gly Pro Asn Cys Gln Thr Pro Ser
    610                 615                 620

Cys Asn Gly Leu Ser Met Ala Lys Tyr Tyr Cys Ser Val Cys Lys Phe
625                 630                 635                 640

Phe Asp Asp Glu Arg Ser Val Tyr His Cys Pro Phe Cys Asn Leu Cys
                645                 650                 655

Arg Leu Gly Gln Gly Leu Gly Ile Asp Phe Phe His Cys Met Lys Cys
            660                 665                 670

Asn Cys Cys Leu Gly Met Lys Leu Ile Glu His Lys Cys Arg Glu Lys
        675                 680                 685

Met Leu Glu Met Asn Cys Pro Ile Cys Cys Asp Phe Leu Phe Thr Ser
    690                 695                 700

Ser Ala Ala Val Lys Gly Leu Pro Cys Gly His Phe Met His Ser Ala
705                 710                 715                 720

Cys Phe Gln Ala Tyr Thr Cys Ser His Tyr Thr Cys Pro Ile Cys Ser
                725                 730                 735

Lys Ser Leu Gly Asp Met Thr Val Tyr Phe Gly Met Leu Asp Gly Leu
            740                 745                 750

Leu Ala Ala Glu Glu Leu Pro Glu Glu Tyr Arg Asp Arg Cys Gln Asp
        755                 760                 765

Ile Leu Cys Asn Asp Cys Glu Arg Lys Gly Arg Ser Arg Phe His Trp
    770                 775                 780

Leu Tyr His Lys Cys Gly Phe Cys Gly Ser Tyr Asn Thr Arg Val Ile
785                 790                 795                 800

Lys Ile Asp Arg Ala Asp Cys Ser Thr Ser Asp
                805                 810
```

<210> SEQ ID NO 3
<211> LENGTH: 3711
<212> TYPE: DNA
<213> ORGANISM: Oryza sativa

<400> SEQUENCE: 3

```
atggcgacgc cgacgcccat ggcggggggag gggacgctcg cggcggtgat gccgcggtcg    60
ccgtccccta cggcttcggc ggcggcgggg tcggcggcgg aggcgccgat gctgatattc   120
ctctacttcc acaaggcgat ccgcgcggag ctcgaggggc tgcacgcggc cgccgtgcgc   180
ctcgccacgg agcgcgccgg cgacgtgggg gcgctcgccg agcgctgccg cttcttcgtc   240
aacatctaca agcaccactg cgacgccgag gacgcggtta tctttccagc acttgatatc   300
cgagtcaaga atgtcgcagg aacctattct cttgagcaca aggggaaaa tgatctcttc     360 agccagctgt ttgctctgtt acagctggac attcaaaatg atgatagtct tcgaagggaa   420
ctcgcatcct gtacaggggc cattcaaaca tgtctctccc aacatatgtc caaagaagaa   480
gagcaggtct ttccattgct tacgaagaaa ttttcatatg aagagcaagc tgatctagtg   540
tggcagttct tatgtaacat tcctgtaaat atgatggcag agttcctccc ctggctttcg   600
tcttcggttt catctgatga acatgaagat atccgtagct gcttatgtaa aatagtacct   660
gaagagaaac tccttcagca ggttgtcttc gcgtggatcg aagggaaaac aacgagaaaa   720
gtaacagaga attccaccaa gtctaattca gaagcaacct gtgattgcaa ggatgcctcc   780
tccattgatc atgcagataa ccatatttct tcacatgaag attctaaagc tgggaacaaa   840
aagtatgcag aatctattga tggtcaggtt gaaaggcatc ccatagatga gattctgtat   900
tggcacaatg ctatccgtaa agagttaatt gatatagcag aggagacaag aaggatgcag   960
caatctggaa atttctctga tatatcatct ttcaatgcaa ggctgcagtt tattgcagat  1020
gtgtgcatct ccacagtat tgccgaggat caggttgtgt ttcctgcagt tgatagtgag   1080
ctgtcctttg tgcatgagca tgctgaagaa gagcgccggt ttaacaattt tagatgttta   1140
attcagcaaa tccaaatagc aggagcaaaa tcaactgcac tagacttta ctctgaattg     1200 tgttcacatg ctgatcagat aatggagaca attgagaaac acttctgtga tgaagaaacc  1260
aaggtgcttc ctcaagctag gatgcttttc tctcctgaga agcaaaggca acttctgtat  1320
aaaagtttat gtgtgatgcc actgaagtta ttagaacgtg ttctcccatg gttagtgtcc  1380
aagctgagtg atgaggaggc atcttctttt cttgaaaata tgcgcttggc agcaccatca  1440
tcggaaacag cactggttac ccttttctct ggttgggcat gcaaagctcg ttcagaggac  1500
aaatccaatt ctggggagta cttatgctta acatctggag aaatgagatg cctattggat  1560
gaagttgatg gactggaaaa atgtcggcca ttctgtccat gtgcttcacg tagcaataca  1620
gatgcttctc tgcatccgca gactgaaaat ggttctaggc caggaaagcg aggaaatgat  1680
gcagaatctg ttcctggtac taatggaagt gacttgtctc agactgatga cactgaagca  1740
cgtccatgta gcaaaaaacc ttgctgtatt cctgggttga gagtagaaac tggcaatctt  1800
gctattagtt catcgctggc ttctgcaaag tcatttcgct ctctatcata caattcttct  1860
gctccttcat tatattcaag cctttttcct tgggagacag atgcatcttt atcttgttca  1920
gatggcatat caaggccaat cgatactata ttcaaatttc ataaagcaat tcgcaaggac  1980
ttagagtacc tagatgttga atctggaaag cttattgatg gtgatgagtc ttgtcttcgc  2040
cagttcattg gaagattccg tttattgtgg ggtctttaca gggcacacag taatgctgag  2100
gatgaaattg ttttcctgc tttagaatca agagagacat tgcacaatgt cagtcactcg   2160
tacactcttg accacaagca agaagaacaa ttatttggag atatatctga tgccctcgct  2220
gagctttcgc agctacatga gaggttgacc cacccccaca ttgaagtcag tgaagcagag  2280
aaaaacgatt ttaattcctc tgatgagatt gattggacta gaaagtacaa cgagcttgcc  2340
acaaagcttc aaggaatgtg caagtctatc cgggctgcat tgactaatca tgtccataga  2400
```

```
gaagaacttg agttgtggcc attgtttgat gagcattttt ctgtggagga acaggataag    2460
cttgtaggtc gtataattgg ttcaactggt gctgaggttc tccaatcgat gctaccctgg    2520
gttacttcag cacttactca ggaagagcag aacatgatgc tggatacatg gaaacaggcc    2580
actaagaata caatgtttgg cgagtggcta acgagtggg  ggaagggagc tccgacatca    2640
tctgattctt cagaagaggc atcctctgct ccagaagata gtcatttaca ggacaagatt    2700
gaccagaatg atcagatgtt caagcctgga tggaaggaca tatttcgaat gaaccagagt    2760
gaacttgagg ctgaggtgcg aaaggtttca cgagatccta cacttgaccc aaggcggaag    2820
gcctatctta tccaaaatct catgaccagt cgctggatag ctgctcagca gaagctacca    2880
gagccaaaat cagaagagtg tagtgaaggt gccggtatcc ctggatgtgc tccttcatat    2940
cgagaccagg agaagcaaat atttggttgt gagcactaca aaaggaactg caagcttgtt    3000
gctgcatgct gcaacaagct gttcacttgc agattctgcc atgataaaat tagtgatcat    3060
acgatggaaa ggaaagcgac acaggagatg atgtgcatgg tatgcttaaa agttcaacct    3120
gttggtccaa attgtcaaac tccgtcttgc aatgggctat ccatggcaaa gtattactgt    3180
aacatctgca aattttttga tgatgaaagg actgtttatc attgcccatt ttgtaatttg    3240
tgccgtcttg ggaaaggtct tggtgttgat ttcttccatt gcatgaagtg caattgctgc    3300
cttgggatga aattaacaga acacaaatgc cgggagaaag gctagagac  aaactgtcca    3360
atctgctgtg atttcctatt tacatcaagc gcggcagtta gagctcttcc ctgtggccat    3420
ttcatgcatt cagcttgctt tcaggcatac acttgtagtc actacacttg tcctatctgc    3480
tgcaaatcct tgggagatat ggcggtgtac tttggcatgt tggacgcctt gctggctgct    3540
gaagagcttc ctgaggaata ccgtgatcgg tgtcaggata tactttgtaa tgattgtgaa    3600
agaaaaggga ggtctcgatt tcactggttg taccataaat gcggctcctg tggttcttat    3660
aataccagag ttatcaagac cgatacagca gattgttcta cgccaaacta g             3711

<210> SEQ ID NO 4
<211> LENGTH: 2436
<212> TYPE: DNA
<213> ORGANISM: Oryza sativa

<400> SEQUENCE: 4
atggagaaaa tcgagaggca cttcaaaaat gaggaaacaa aggtacttcc tcaagctagg      60
attcattttt catcagagaa acaaagggaa cttttatata agagtctctg tgtcataccg     120
ttgaagttat tggagcgtgt tttaccgtgg tttgtatcga agctgaatga tcaggatgca     180
gaagcttttc ttcagaatat gttttttggca gcaccttcct ctgaagctgc attggtcact    240
cttctctctg gttgggcatg caaaggtcgc tcaaagggca cctctaactc tggaaaattc    300
atatgcttga caccaagggc actgagcagc ccattggatg aaaatgggtt taaagactgc    360
cagttatgtc catgttcttt acaatcagat atttgttcta ggccagccaa gaaatggaat    420
gacacagaat ctagtaacat aagcaactgc tcacaaacgg ctgatatagc attgacatgt    480
aaaaacagac cttgtcacat tcctgggtta agggtagaaa ttagcaatct tgctgtcaat    540
tcgtttgctt ctgcagagtc cttccgatcg ctgtctctca attattctgc tccttcattg    600
tattcaagtc ttttttcatg ggagacagat gcagcctttt ctggcccaga taacatttca    660
aggccaattg acacaatatt caaatttcat aaggcaattc gcaaagattt ggagttctta    720
gatgtggaat ctagaaaagct catagatggg gatgaatctt cccttcgcca attcatcgga    780
```

```
aggtttcgtt tactgtgggg tctttataga gcacacagca atgctgaaga tgaaattgta    840
tttcctgctc ttgaatcgaa agagacactg cacaatgtca gccactcata tactcttgac    900
cacaagcagg aagaagaatt atttaaagat atatccacta ttcttttga gctttcacaa     960 ttgcatgctg atttgaagca tcctcttggt ggtgctgatg cagttggagc gaaccacatt   1020
catccatata ataggatcga ttggtccaaa agaataatg aacttttgac aaagcttcaa    1080
ggaatgtgca agtctatccg ggttactctg tctaatcatg tccatagaga gaacttgaa    1140 ttgtggccac tatttgataa acattttct gtagaggagc aggataagat tgtaggccgt    1200
ataattggaa gtacaggagc tgaggttctg cagtcaatgt taccctgggt tacatcagcg   1260
cttagtctag atgaacagaa caatatgctg gacacatgga ggcaagtaac taagaataca   1320
atgtttgatg aatggctaaa tgaatggtgg aagagatcac ctacttcttc tggcccttca   1380
agcgatgcct cccatccaga agaagatcat ttccaggaaa agttcgatca gagtgaacag   1440
atgtttaagc ctggttggaa ggacatcttc cgaatgaacc agagtgagct tgaggctgag   1500
atacgaaagg tttctcgtga ttctactctt gacccaagga ggaaggctta tctaatccaa   1560
aatctcatga ccagccgctg gatagctgct cagcagaaat cgccccaacc tcagtcagaa   1620
gatcgcaatg atgtacagt attacctgga tgttgtcctt cataccggga tccagagaat   1680 cagattttg ctgtgagca ttacaaaagg aaatgcaaac ttgttgctgc atgctgcaat    1740
aaactgttca catgcaggtt ttgtcatgat aaagttagtg accatacaat ggaaaggaaa   1800
gcaacggtgg aaatgatgtg catgcaatgc ctgaaagttc aaccagttgg tccaaattgc   1860
cagacccctt cttgcaatgg gctatccatg gcaaagtatt attgcagcgt atgcaagttt   1920
tttgacgatg aaaggagtgt gtaccattgc ccctttttgca atttgtgtcg tcttgggcaa   1980
ggattgggta ttgatttttt ccattgcatg aagtgcaact gttgcctggg catgaaattg   2040
atagagcata atgtcgaga aaagatgcta gagatgaatt gcccaatctg ctgcgacttc    2100
ctatttacat cgagtgcagc agttaaaggt ctaccttgtg gccatttcat gcattcagct   2160
tgctttcagg cgtacacctg tagtcactac acctgcccaa tctgctctaa atccttggga   2220
gatatgacag tatactttgg catgcttgat ggcttgctgg ccgcagaaga gcttcctgag   2280
gaataccggg accggtgcca ggatatactt tgtaacgatt gtgaaagaaa aggaaggtct   2340
cggttccatt ggctgtatca caaatgcggc ttctgcggtt catataacac tagagttatc   2400
aagattgata gagctgattg ttcaacatca gattaa                             2436
```

<210> SEQ ID NO 5
<211> LENGTH: 335
<212> TYPE: DNA
<213> ORGANISM: Artificial Sequence
<220> FEATURE:
<223> OTHER INFORMATION: Description of Artificial Sequence: OsHRZ2
      partial coding region and whole 3'UTR sequence.

<400> SEQUENCE: 5

```
cacctgccca atctgctcta atccttggga agatatgaca gtatactttg gcatgcttga     60
tggcttgctg gccgcagaag agcttcctga ggaataccgg gaccggtgcc aggatatact    120
ttgtaacgat tgtgaaagaa aaggaaggtc tcggttccat tggctgtatc acaaatgcgg    180
cttctgcggt tcatataaca ctagagttat caagattgat agagctgatt gttcaacatc    240
agattaacca ggcgagattt tccctctcat attcgaaatt ccttttgaat atatatattg    300
ttgtaaatat acatcaactt aaagaaatcc atgcg                                335
```

IRON-ZINC BINDING CONTROL FACTOR, AND TECHNIQUE FOR IMPROVING IRON DEFICIENCY TOLERANCE OF PLANT AND ENHANCING IRON AND ZINC ACCUMULATION IN EDIBLE PART THEREOF BY CONTROLLING EXPRESSION OF NOVEL IRON-ZINC BINDING CONTROL FACTOR

CROSS REFERENCE TO RELATED APPLICATIONS

This patent application is a U.S. national stage application under 35 U.S.C. §371 of International Patent Application No. PCT/JP2013/069628 filed on Jul. 19, 2013, which claims the benefit of foreign priority to Japanese Patent Application No. JP 2012-166233 filed on Jul. 26, 2012, the disclosures of all of which are hereby incorporated by reference in their entireties. The International Application was published in Japanese on Jan. 30, 2014, as International Publication No. WO 2014/017394 A1 under PCT Article 21(2).

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

The sequence listings disclosed in the ASCII text file submitted herewith, named "seqlist.txt" and created on Oct. 3, 2014, the size of which is 26,116 bytes, are hereby incorporated by reference.

TECHNICAL FIELD

The present invention relates to improvement of iron deficiency tolerance of a plant, and enhancement of iron and zinc accumulation in an edible part thereof. In particular, it relates to a protein, a gene, a vector, a transformant, a gene-disrupted strain, and an antibody that act to control iron deficiency tolerance of a plant, and iron and zinc accumulation in an edible part thereof a method of constructing a plant with improved iron deficiency tolerance, and enhanced iron and zinc accumulation in an edible part thereof; a composition for constructing a plant with improved iron deficiency tolerance, and enhanced iron and zinc accumulation in an edible part thereof; a kit for constructing a plant with improved iron deficiency tolerance, and enhanced iron and zinc accumulation in an edible part thereof; and a method of breeding a plant with improved iron deficiency tolerance, and enhanced iron and zinc accumulation in an edible part thereof.

Priority is claimed on Japanese Patent Application No. 2012-166233, filed Jul. 26, 2012, the content of which is incorporated herein by reference.

BACKGROUND ART

Iron and zinc are necessary for plant growth, carbon fixation and material production. Plants utilize the iron and zinc in soil by absorbing them.

However, there is little solubilized iron and zinc in the calcareous alkaline soil accounting for approximately 30% of soil worldwide, and the amount of solubilized iron therein is extremely low. Consequently, iron deficiency is a principal limiting factor with respect to plant growth in calcareous alkaline soil.

For this reason, it is an urgent task to acquire plants that grow satisfactorily even in poor soil, and especially in calcareous alkaline soil.

Plants which absorb iron and zinc from soil are principal supply sources of minerals for humans. As iron deficiency disorder and zinc deficiency disorder are grave problems for the world's population, and particularly for children and women, it would be desirable to acquire plants that contain copious amounts of iron and zinc in their edible parts.

In recent years, identification and analysis of genes that contribute to absorption and utilization of iron and zinc (particularly iron) have advanced. By altering such genes, and introducing them into plants, plants are being acquired that have improved iron and zinc deficiency tolerance, or which abundantly accumulate iron and zinc in their edible parts (see, e.g., Non-Patent Documents 1-11).

PRIOR ART DOCUMENTS

Non-Patent Documents

Non-Patent Document 1: Takahashi, M., et. al., Nature Biotech., (2001) vol. 19, pp. 466-469.
Non-Patent Document 2: Ishimaru, Y., et. al., Proc. Natl. Acad. Sci. USA, (2007) vol. 104, pp. 7373-7378.
Non-Patent Document 3: Suzuki, M., et. al., Soil Sci. Plant Nutr., (2008) vol. 54, pp. 77-85.
Non-Patent Document 4: Ogo, Y., et. al., Plant Mol. Biol., (2011) vol. 75, pp. 593-605.
Non-Patent Document 5: Goto, F., et. al., Nature Biotech., (1999) vol. 17, pp. 282-286.
Non-Patent Document 6: Uauy, C., et. al., Science, (2006) vol. 314, pp. 1298-1301.
Non-Patent Document 7: Masuda, H., et. al., Rice, (2008) vol. 1, pp. 100-108.
Non-Patent Document 8: Masuda, H., et. al., Rice, (2009) vol. 2, pp. 155-166.
Non-Patent Document 9: Lee, S., et. al., Proc. Natl. Acad. Sci. USA, (2009) vol. 106, pp. 22014-22019.
Non-Patent Document 10: Wirth, J., et. al., Plant Biotech. J., (2009) vol. 7, pp. 1-14.
Non-Patent Document 11: Ishimaru, Y., et. al., Plant J., (2010) vol. 62, pp. 379-390.

DISCLOSURE OF INVENTION

Problems that the Invention is to Solve

However, with respect to calcareous soil, no plants have been acquired which exhibit growth equivalent or superior to growth in good soil. Moreover, no plants have been acquired which are capable of accumulating large amounts of iron and/or zinc (e.g., twice or more of conventional amounts) in both calcareous soil and good soil.

Accordingly, there is still room for improvement with respect to acquiring plants that have such properties.

The present invention was made in light of the foregoing circumstances, and provides a transformant and a gene-disrupted strain which exhibit better growth in calcareous soil than ordinary plants, and which are capable of accumulating larger amounts of iron and zinc in edible parts thereof in both calcareous soil and good soil; a gene, a vector, a protein, and an antibody which are used for constructing the transformant and the gene-disrupted strain; a method of constructing a plant which has improved iron deficiency tolerance, and enhanced iron and zinc accumulation in an edible part thereof; a composition for constructing a plant which has improved iron deficiency tolerance, and enhanced iron and zinc accumulation in an edible part thereof; a kit for constructing a plant which has improved iron deficiency tolerance, and enhanced iron and zinc accumulation in an edible part thereof; and a method of breeding a plant which has improved iron deficiency tolerance, and enhanced iron and zinc accumulation in an edible part thereof. An edible part may refer, for example, to a seed, an aerial part, a stem, a leaf, a root, or the like of a plant, but one is not necessarily limited to these parts provided that it is a part that may be consumed as food or feed. In the case where the aforementioned plant is rice, as the part corresponding to seed, one may cite unpolished rice, and what is obtained by polishing this, such as rice with the germ, partially polished rice, and polished rice.

Means for Solving the Problems

As a result of diligent research aimed at solving the aforementioned problems, the present inventors discovered proteins that act to suppress iron deficiency response in plants. By constructing plants in which expression of the genes that encode the proteins are suppressed, they discovered that the iron deficiency tolerance of the plants can be improved, and iron and zinc accumulation in edible parts thereof can be enhanced, thereby perfecting the present invention.

That is, the present invention provides a protein, a gene, a vector, a transformant, a gene-disrupted strain, and an antibody having the below-mentioned characteristics; a method of constructing a plant that has improved iron deficiency tolerance, and enhanced iron and zinc accumulation in an edible part thereof; a composition for constructing a plant that has improved iron deficiency tolerance, and enhanced iron and zinc accumulation in an edible part thereof; a kit for constructing a plant that has improved iron deficiency tolerance, and enhanced iron and zinc accumulation in an edible part thereof; and a method of breeding a plant that has improved iron deficiency tolerance, and enhanced iron and zinc accumulation in an edible part thereof.

(1) A protein, which is an iron- and zinc-binding regulatory factor, and which includes any one of the following amino acid sequences of (a) to (c):

(a) an amino acid sequence represented by SEQ ID NO:1 or 2;

(b) an amino acid sequence obtained by deletion, substitution, or addition of one to several amino acids in the amino acid sequence represented by SEQ ID NO:1 or 2; or (c) an amino acid sequence which has 80% or more identity with the amino acid sequence represented by SEQ ID NO:1 or 2.

(2) A gene, which encodes the protein of (1) above.

(3) A gene, which encodes a protein that is an iron- and zinc-binding regulatory factor, and which includes any one of the following DNA of (d) to (g):

(d) DNA composed of a base sequence represented by SEQ ID NO:3 or 4;

(e) DNA composed of a base sequence obtained by deletion, substitution, or addition of one to several bases in the base sequence represented by SEQ ID NO:3 or 4;

(f) DNA composed of a base sequence that has 80% or more identity with the base sequence represented by SEQ ID NO:3 or 4; or (g) DNA composed of a base sequence capable of hybridizing under stringent conditions with DNA including a complementary base sequence to DNA composed of the base sequence represented by SEQ ID NO:3 or 4.

(4) A vector, which is capable of suppressing expression of the gene of (2) or (3) above.

(5) The vector of (4) above, which is capable of expressing RNAi-inducing nucleic acid that can suppress expression of the aforementioned gene on an mRNA level.

(6) The vector of (5) above, wherein the aforementioned RNAi-inducing nucleic acid is a base sequence represented by SEQ ID NO:5.

(7) A transformant, obtained by introducing any one of the vectors of (4) to (6) above into a host.

(8) A gene-disrupted strain, having genomic DNA in which the gene of (2) or (3) above is disrupted by incorporation of an inserted sequence.

(9) An antibody, which specifically binds with the protein of (1) above.

(10) A method of constructing a plant with improved iron deficiency tolerance, and enhanced iron and zinc accumulation in an edible part of the plant, the method including a step for introducing any one of the vectors of (4) to (6) above into the plant.

(11) A composition for constructing a plant with improved iron deficiency tolerance, and enhanced iron and zinc accumulation in an edible part of the plant, the composition including any one of the vectors of (4) to (6) above.

(12) A kit for constructing a plant with improved iron deficiency tolerance, and enhanced iron and zinc accumulation in an edible part of the plant, the kit including any one of the vectors of (4) to (6) above.

(13) A method for breeding a plant with improved iron deficiency tolerance, and enhanced iron and zinc accumulation in an edible part of the plant, the method including a step that detects the protein of (1) above contained in a liquid extract from the plant.

(14) A method for breeding a plant with improved iron deficiency tolerance, and enhanced iron and zinc accumulation in an edible part of the plant, the method including a step that detects the gene of (2) or (3) above contained in a liquid extract from the plant.

Effects of the Invention

According to the present invention, it is possible to construct a transformant and a gene-disrupted strain, which exhibit better growth than ordinary plants in calcareous soil, and which are capable of accumulating large amounts of iron and zinc in both calcareous soil and good soil.

Furthermore, according to the present invention, it is possible to contribute to carbon fixation and material production in poor soil, and alleviation of human iron and zinc deficiency disorders.

BRIEF DESCRIPTION OF THE DRAWINGS

FIG. 4 illustrates analytic results concerning expression levels of mRNA of OsHRZ1 and OsHRZ2 obtained using quantitative RT-PCR.

FIG. 20 illustrates accumulated iron concentrations in seeds of OsHRZ-disrupted strains obtained by pot cultivation in normal soil.

FIG. 21 illustrates accumulated zinc concentrations in seeds of OsHRZ-disrupted strains obtained by pot cultivation in normal soil.

FIG. 24 illustrates analytic results of gene expression profiles obtained using a 44K microarray for roots of OsHRZ2 expression-suppressed strains that underwent hydroponic cultivation under iron-sufficient conditions and iron-deficient conditions.

MODES FOR CARRYING OUT THE INVENTION

<OsHRZ Proteins>

The protein of the present invention includes any one of the amino acid sequences of (a)-(c) below, and is an iron- and zinc-binding regulatory factor.

(a) an amino acid sequence represented by SEQ ID NO:1 or 2;

(b) an amino acid sequence obtained by deletion, substitution, or addition of one to several amino acids in the amino acid sequence represented by SEQ ID NO:1 or 2; or (c) an amino acid sequence which has 80% or more identity with the amino acid sequence represented by SEQ ID NO:1 or 2.

The amino acid sequence of (a) above is an amino acid sequence represented by SEQ ID NO:1 or 2.

The present inventors have named the proteins composed of amino acid sequences represented by SEQ ID NO:1 and 2 "*Oryza sativa* Hemerythrin motif-containing Really Interesting New Gene (RING)- and Zinc-finger protein (hereinafter OsHRZ) 1" and "OsHRZ2", respectively.

Figure 1:
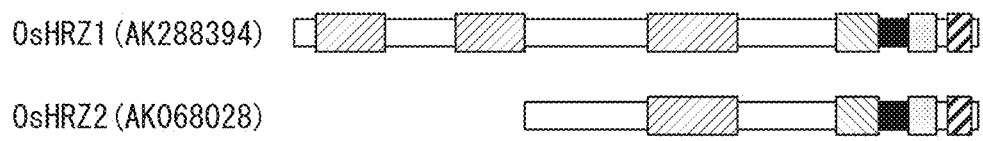
FIG. 1 illustrates domain structures of OsHRZ1 and OsHRZ2 proteins of the present invention.

As shown in FIG. 1, from the N terminal side to the C terminal side, OsHRZ1 includes three putative hemerythrin (also known as "HHE") domains, two zinc-finger domains that are presumed to contribute to transcriptional regulation, post-transcriptional regulation, regulation of protein degradation, and the like (a CHY-type zinc-finger domain and a CTCHY-type zinc-finger domain), a RING zinc-finger domain that functions as an E3 ligase, and that contributes to regulation of protein degradation, and a Rubredoxin-type motif that is presumed to form iron-sulfur clusters for purposes of electron transfer.

As shown in FIG. 1, from the N terminal side to the C terminal side, OsHRZ2 includes a single hemerythrin domain, three zinc-finger domains (a CHY-type zinc-finger domain, a CTCHY-type zinc-finger domain, and a RING zinc-finger domain), and a Rubredoxin-type motif.

During cultivation under iron-deficient conditions, expression of the genes that encode these OsHRZ proteins is induced.

OsHRZ proteins synthesized in plants are thought to bind with iron and zinc via hemerythrin domains, and to function as iron sensors that detect concentration ratios of iron and other metals in plant cells.

Furthermore, the OsHRZ1 and OsHRZ2 proteins suppress expression of iron uptake-related genes and iron translocation-related genes mainly in cultivation under iron-sufficient conditions via the aforementioned three zinc-finger domains that are presumed to contribute to transcriptional regulation, post-transcriptional regulation, regulation of protein degradation, and the like.

As the aforementioned (b), for example, one may cite a protein which has a mutation (deletion, insertion, substitution, or addition) at a site other than the hemerythrin domains, or a protein which has a mutation in a hemerythrin domain that maintains iron- and zinc-binding activities.

As the aforementioned (b), one may also cite, for example, a protein which has a mutation at a site other than the aforementioned three zinc-finger domains that are presumed to contribute to transcriptional regulation, post-transcriptional regulation, regulation of protein degradation, and the like, or a protein which has a mutation in the aforementioned zinc-finger domains that maintains an ability to suppress expression of iron uptake-related genes and iron translocation-related genes.

Now, with respect to the number of amino acids that may be deleted, substituted, or added, 1-10 is preferable, 1-7 is more preferable, 1-5 is still more preferable, 1-3 is particularly preferable, and 1-2 is most preferable.

In the amino acid sequences forming the protein of the present invention, introduction of a mutation into one to several amino acids is easily conducted using conventional technology.

For example, according to the conventional point mutation introduction method, it is possible to cause mutation in an arbitrary base in a gene that encodes a protein. It is also possible to produce a deletion mutation or an addition mutation by designing a primer corresponding to an arbitrary site in a gene that encodes a protein.

As the aforementioned (c), for example, one may cite a protein which has a mutation (deletion, insertion, substitution, or addition) at a site other than a hemerythrin domain, or a protein which has a mutation in a hemerythrin domain that maintains iron- and zinc-binding activities.

As the aforementioned (c), for example, one may also cite a protein which has a mutation at a site other than the aforementioned three zinc-finger domains that are presumed to contribute to transcriptional regulation, post-transcriptional regulation, regulation of protein degradation, and the like, or a protein which has a mutation in the aforementioned zinc-finger domains that maintains an ability to suppress expression of iron uptake-related genes and iron translocation-related genes.

Now, with respect to homology (identity of amino acid sequence) with the amino acid sequence represented by SEQ ID NO:1 or 2, 80% or more is preferable, 85% or more is more preferable, 90% or more is still more preferable, 95% or more is particularly preferable, and 98% or more is most preferable.

With respect to the expression vector used to express the protein of the present invention, one may cite a cell vector that causes the protein of the present invention to be expressed in a host cell, and a cell-free vector that causes the protein of the present invention to be expressed in a protein translation system including components that have a protein synthesizing function and that are extracted from suitable cells.

As a cell vector, a conventional expression vector suited to the host cell may be used. For example, with respect to *Escherichia coli*, one may cite ColEI type plasmid represented by pBR322 derivative, pACYC plasmid with p15A origin, pSC plasmid, and F factor-derived mini F plasmid such as Bac. In addition, one may also cite an expression vector having a tryptophan promoter such as trc and tac, lac promoter, T7 promoter, T5 promoter, T3 promoter, SP6 promoter, arabinose-inducible promoter, cold shock promoter, tetracycline-inducible promoter, and so on.

As a cell-free vector, one may cite an expression vector having the T7 promoter or an expression vector having the T3 promoter referenced among cell vectors; a cell-free wheat protein synthesizing vector such as pEU plasmid that has SP6 promoter or T7 promoter; and so on.

In protein synthesis using a cell-free vector, first, cDNA is transcribed using a transcription system, and mRNA is synthesized. As the pertinent transcription system, a conventional one may be cited that causes transcription by RNA polymerase. As RNA polymerase, one may cite, for example, T7 RNA polymerase.

Next, the mRNA is translated using a cell-free protein synthesizing system that is a translation system, and the protein is synthesized. The system includes elements required for translation such as ribosomes, translation initiation factors, translation elongation factors, dissociating factors, and aminoacyl-tRNA synthetases. As such a protein translation system, one may cite liquid *E. coli* extract, liquid rabbit reticulocyte extract, liquid wheat germ extract, and so on.

One may also cite a reconstituted cell-free protein synthesizing system composed of factors obtained by independently purifying the elements required in the aforementioned translation.

Protein synthesized using cell vectors or cell-free vectors may be used in cell extract, but can also be purified for use. As a purification method, one may cite the salting-out method, or a method using any of various types of chromatography. In the case where an expression vector is designed to express a tag sequence such as a histidine tag at the N terminal or the C terminal of a target protein, one may cite the purification method of an affinity column which uses a substance such as nickel or cobalt that is compatible with this tag. Otherwise, the purity of the protein of the present invention can be raised by conducting purification in appropriate combinations, e.g., by combining ion exchange chromatography and gel filtration chromatography.

<OsHRZ Genes>

The gene of the present invention encodes any one of the amino acid sequences of (a) to (c) above, and encodes a protein that is an iron- and zinc-binding regulatory factor.

In addition, the gene of the present invention includes any one DNA of (d) to (g) below, and encodes a protein that is an iron- and zinc-binding regulatory factor:

(d) DNA composed of a base sequence represented by SEQ ID NO:3 or 4;

(e) DNA composed of a base sequence obtained by deletion, substitution, or addition of one to several bases in the base sequence represented by SEQ ID NO:3 or 4;

(f) DNA composed of a base sequence, wherein identity with the base sequence represented by SEQ ID NO:3 or 4 (homology with the base sequence) is 80% or more, preferably 85% or more, more preferably 90% or more, still more preferably 95% or more, and most preferably 98% or more; or (g) DNA composed of a base sequence capable of hybridizing under stringent conditions with DNA including a complementary base sequence to DNA composed of the base sequence represented by SEQ ID NO:3 or 4.

Now, with respect to the number of bases that may be deleted, substituted, or added, 1-30 is preferable, 1-20 is more preferable, 1-15 is still more preferable, 1-10 is particularly preferable, and 1-5 is most preferable.

In the present invention and in the present Specification, "under stringent conditions" signifies, for example, the method recorded in "Molecular Cloning—A Laboratory Manual, Third Edition" (Sambrook et al., Cold Spring Harbor Laboratory Press). For example, one may cite conditions where hybridization is performed by conducting incubation at 55-70° C. over a period from several hours to overnight in a hybridization buffer including 5×SSC (composition of 20×SSC: 3 M sodium chloride, 0.3 M citric acid solution, pH 7.0), 0.1 weight % N-lauroyl sarcosine, 0.02 weight % SDS, 2 weight % blocking reagent for nucleic acid hybridization, and 50% formamide. As a washing buffer used when conducting washing after incubation, a 1×SSC solution containing 0.1 weight % SDS is preferable, and a 0.1×SSC solution containing 0.1 weight % SDS is more preferable.

<OsHRZ Gene Expression Suppression Vector>

The vector of the present invention is capable of suppressing expression of the above-described genes of the present invention. The vector of the present invention preferably enables expression of RNAi-inducing nucleic acid that is capable of suppressing expression of the aforementioned genes at the mRNA level.

RNAi-inducing nucleic acid signifies nucleic acid that is capable of inducing RNA interference by introduction into a plant cell. RNA interference signifies an effect where RNA including a base sequence that is complementary with mRNA (or a partial sequence thereof) suppresses expression of the mRNA.

The mRNA targeted by RNAi-inducing nucleic acid may be a coding region, or a non-coding region. As the aforementioned RNAi-inducing nucleic acid, a base sequence represented by SEQ ID NO:5 is preferable, and this RNAi-inducing nucleic acid targets the entire length of 3'UTR (untranslated region) and part of the coding region of OsHRZ.

As RNAi-inducing nucleic acid, one may cite, for example, siRNA or miRNA. As a vector that is introduced into a plant cell, and that induces RNAi in the same manner as siRNA, one may cite the shRNA (short hairpin RNA/small hairpin RNA) expression vector.

According to the vector of the present invention, it is possible to improve the iron deficiency tolerance and the iron and zinc accumulation of a plant.

Here, "iron deficiency tolerance of a plant" signifies a characteristic of enabling growth even in soil that has little solubilized iron content, and signifies a characteristic of inhibiting occurrence of, for example, an iron deficiency disorder called "chlorosis" (yellowing due to chlorophyll deficiency) in alkaline soil.

"Iron and zinc accumulation" signifies a characteristic of enabling accumulation of high concentrations of iron and zinc in the above-ground part of rice, and particularly in the seed that is an edible part thereof. For example, seed obtained by cultivating a transformant that was constructed using the aforementioned vector in ordinary soil in an isolation field (signifies an isolation field for genetic recombination prepared based on a prescribed procedure) has approximately 3.8 times more iron content and approximately 1.2 times more zinc content than non-treated rice seed.

The vector of the present invention may be constructed by a conventional genetic recombination technique.

<Transformant, and Method of Constructing a Plant with Improved Iron Deficiency Tolerance, and Iron and Zinc Accumulation>

The transformant (also referred to as "expression-suppressed strain") of the present invention is constituted by introducing the vector of the present invention into a host. As stated above, the vector of the present invention is able to improve the iron deficiency tolerance and the iron and zinc accumulation of a host plant. Consequently, the transformant of the present invention has excellent iron deficiency tolerance, and can accumulate high concentrations of iron and zinc, particularly in edible parts.

The method of the present invention for constructing a plant with improved iron deficiency tolerance and iron and zinc accumulation signifies a method for preparing a plant body with improved iron deficiency tolerance and iron and zinc accumulation. There are no particular limitations on the method of the present invention for constructing a plant with improved iron deficiency tolerance and iron and zinc accumulation, provided that it includes a step that introduces the vector of the present invention into a plant body.

In the case where a recombinant expression vector is used, there are no particular limitations on the vector to be used in transformation of a plant body, provided that it is a vector capable of suppressing expression of the gene of the present invention in the plant.

As such a vector, one may cite, for example, a vector having a promoter that constitutively expresses the gene in a plant cell, such as the 35S promoter of cauliflower mosaic virus; and a vector having a promoter that is activated into having induction properties by external stimuli.

Plants subject to transformation under the present invention signify whichever of an entire plant body, a plant organ (e.g., leaf, petal, stem, root, and seed), plant tissue (e.g., epidermis, phloem, parenchyma, xylem, vascular bundle, palisade tissue, and spongy tissue), or plant cultured cells or plant cells in various forms (e.g., suspended cultured cells), protoplast, leaf segments, callus, and so on. There are no particular limitations on the plant used in transformation, but poaceae plants are preferable, and rice, barley, wheat, and corn are more preferable.

To introduce the gene into a plant, transformation methods familiar to those skilled in the art (e.g., *Agrobacterium* method, gene gun, PEG method, and electroporation method) are used, and are roughly divided into methods that are mediated by *Agrobacterium*, and methods that conduct introduction directly into plant cells. In the case where an *Agrobacterium* technique is used, a method may be employed which obtains a transformed plant by introducing the constructed expression vector for the plant into a suitable *Agrobacterium* (e.g., *Agrobacterium tumefaciens*), and infecting a sterile cultured leaf disc with this strain according to the leaf disc method (Hirofumi Uchimiya, Plant Gene Manipulation Manual (1990), pp. 27-31, Kodansha Scientific, Tokyo), or the like.

It is also possible to use the method of Nagel et al. (Microbiol. Lett., (1990) vol. 67, pp. 325). This is a method which first introduces the expression vector into *Agrobacterium*, and then introduces the transformed *Agrobacterium* into a plant cell or plant tissue by a method recorded in Plant Molecular Biology Manual (S. B. Gelvin et al., Academic Press Publishers). Here, "plant tissue" includes callus obtained by culture of plant cells. In the case where transformation is conducted using an *Agrobacterium* technique, it is possible to use pBI binary vectors (e.g., pBIG, pBIN19, pBI101, pBI121, pBI221, and pPZP202).

As a method for directly introducing a gene into a plant cell or plant tissue, one may cite the electroporation method, the gene gun method, and so on. In the case where a gene gun is used, a plant body, plant organ, or plant tissue itself may be used without alteration as the subject of gene introduction, and may be used after preparing a section, or may be used with preparation of protoplast. A sample prepared in this manner can be treated using a gene introduction device (e.g., PDS-1000 (manufactured by BIO-RAD Corp.)). Treatment conditions vary according to plant or sample, but treatment is normally conducted at a pressure of 450-2000 psi, and at a distance of 4-12 cm.

The cell or plant tissue into which the gene is introduced is first selected by drug resistance such as hygromycin resistance, and is then regenerated to a plant body by a conventional method. Regeneration of a plant body from a transformed cell can be conducted by a method known to persons skilled in the art according to the type of plant cell. The selection marker is not limited to hygromycin resistance, and one may also cite, for example, drug resistance such as bleomycin resistance, kanamycin resistance, gentamicin resistance, chloramphenicol resistance, and so on.

In the case where plant culture cells are used as the host, one may cite, for example, the microinjection method, electroporation method, polyethylene glycol method, gene gun (particle gun) method, protoplast fusion method, calcium phosphate method, and so on. By means of these methods, a recombination vector is introduced into cultured cells, and transformed. A callus, shoot, capillary root or the like obtained as a result of transformation can be used without alteration in cell culture, tissue culture, or organ culture. These can be regenerated to a plant body by administering plant hormones (auxin, cytokinin, gibberellin, abscisic acid, ethylene, brassinolide, and the like) in a suitable concentration, using a known plant tissue culture method.

Confirmation regarding whether or not the gene was introduced into the plant can be conducted by the PCR method, Southern hybridization method, Northern hybridization method, or the like. For example, PCR is conducted by preparing DNA from a transformed plant, and by designing a DNA-specific primer. PCR can be conducted under conditions known to persons skilled in the art. Subsequently, agarose gel electrophoresis, polyacrylamide gel electrophoresis, capillary electrophoresis, or the like is conducted with respect to the amplified product, and staining is conducted by ethidium bromide, SYBR Green solution, or the like. Occurrence of transformation can then be confirmed by detecting the amplified product as one band. Or the amplified product can also be detected by conducting PCR using a primer labeled in advance by fluorochrome or the like. Furthermore, it is also possible to adopt a method that binds the amplified product to the solid phase of a microplate or the like, and that confirms the amplified product by fluorescence or an enzyme reaction.

Once the transformed plant that has incorporated the vector of the present invention into the genome is acquired, offspring can be obtained by sexual reproduction or asexual reproduction of the plant body. From the aforementioned plant body or its offspring or clones thereof, it is possible to obtain, for example, seed, fruit, cut ear, tuber, tuberous root, rootstock, callus, protoplast, and the like, and mass-produce the aforementioned plant body based thereon.

Therefore, the transformant of the present invention also includes a plant body into which the vector of the present invention has been expressibly introduced, or offspring of the aforementioned plant body having the same properties as the plant body, or tissue derived from these.

<Gene-Disrupted Strain>

Figure 2:
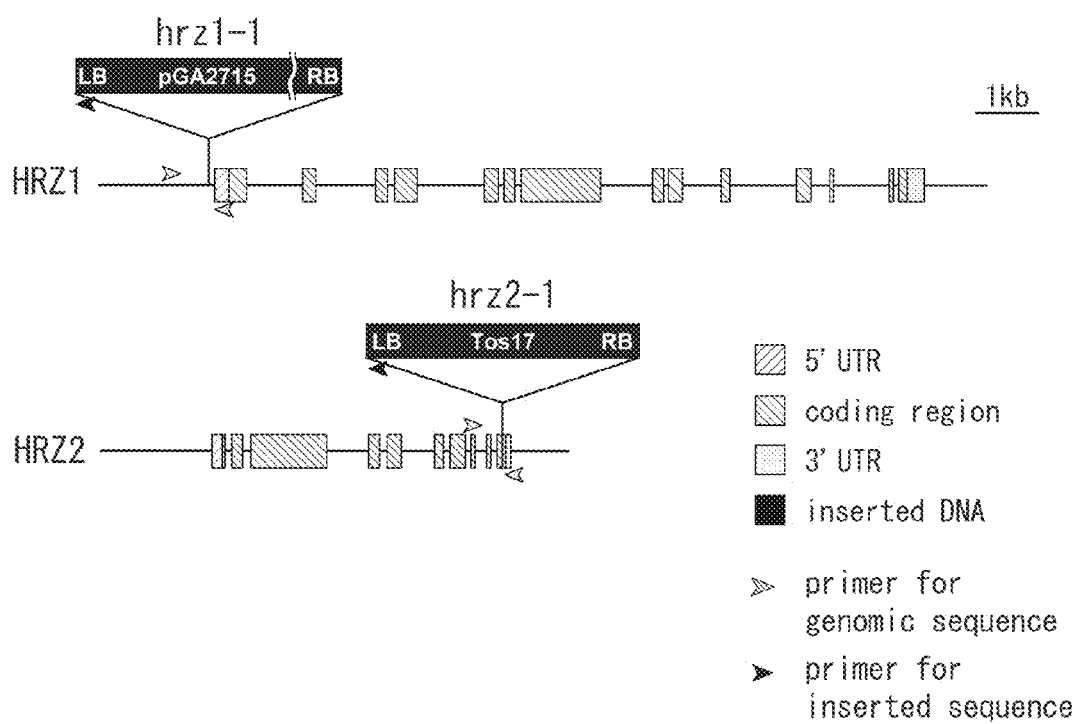
FIG. 2 illustrates genomic structures in the gene-disrupted strains of the present invention.

The gene-disrupted strain of the present invention has genomic DNA in which the gene of the present invention is disrupted by incorporation of an inserted sequence. For example, as shown in FIG. 2, by inserting T-DNA (hrz1-1) into genomic DNA by homologous recombination, or by transpositioning a transposon (hrz2-1), the gene of the present invention existing on genomic DNA is disrupted, and its expression is suppressed.

According to the gene-disrupted strain of the present invention, expression of the gene and the protein of the present invention are suppressed. Consequently, constitutive suppression of expression of iron uptake-related genes and iron translocation-related genes is canceled, enabling improvement of iron deficiency tolerance and iron and zinc accumulation in a plant.

As the gene-disrupted strain of the present invention, the Tos17-insertion strain ND6059 (Rice Genome Resource Center) is preferable. As it is not a transformed plant, this inserted strain is superior from the standpoint that it can be grown quickly in ordinary agricultural fields.

As stated above, in addition to being provided with conspicuously improved iron and zinc accumulation in an edible part thereof, the transformant and the gene-disrupted strain of the present invention are also endowed with excellent iron deficiency tolerance. Consequently, they are particularly useful for stably producing iron-enriched foods under cultivation conditions that have a latent tendency to lapse into iron deficiency, as in semi-arid regions, calcareous soil, and the like.

<Composition for Constructing a Plant with Improved Iron Deficiency Tolerance and Iron and Zinc Accumulation, and Construction Kit>

The composition of the present invention for constructing a plant with improved iron deficiency tolerance and iron and zinc accumulation includes the vector of the present invention. Moreover, the kit of the present invention for constructing a plant with improved iron deficiency tolerance and iron and zinc accumulation is provided with the vector of the present invention. Here, "composition" signifies a form where all of the various ingredients are contained in a single substance. "Kit" signifies a form where at least one of the various ingredients is contained in a separate substance.

A "composition for constructing a plant with improved iron deficiency tolerance and iron and zinc accumulation" is a composition used for the purpose of preparing a plant body that has improved iron deficiency tolerance and iron and zinc accumulation. A "kit for constructing a plant with improved iron deficiency tolerance and iron and zinc accumulation" is a kit used for the purpose of preparing a plant with improved iron deficiency tolerance and iron and zinc accumulation.

The transformant of the present invention is constituted by introducing the vector of the present invention into a host (plant). By this means, expression of the gene of the present invention is suppressed, enabling improvement of iron deficiency tolerance and iron and zinc accumulation. If the vector of the present invention is used, the vector of the present invention can then be introduced into a plant body as described above. Therefore, a composition provided with the vector of the present invention, or a kit provided with the vector can be used to good effect for the purpose of constructing a plant with improved iron deficiency tolerance and iron and zinc accumulation.

That is, the composition of the present invention for constructing a plant with improved iron deficiency tolerance and iron and zinc accumulation, or the kit for constructing a plant with improved iron deficiency tolerance and iron and zinc accumulation can be used as a vector supply source in the above-described method of the present invention for constructing a plant with improved iron deficiency tolerance and iron and zinc accumulation.

In addition to the vector of the present invention, the composition of the present invention for constructing a plant with improved iron deficiency tolerance and iron and zinc accumulation may also be provided with a solvent, a dispersion medium, a reagent, and so on.

In addition to the vector of the present invention, the kit of the present invention for constructing a plant with improved iron deficiency tolerance and iron and zinc accumulation may also be provided with a solvent, a dispersion medium, a reagent, written instructions for use thereof, and so on. Now, with respect to the kit of the present invention, apart from the written instructions, being "provided with" a solvent and so on signifies that it is contained within any one of the individual containers (e.g., bottles, plates, tubes, dishes, or the like) constituting the kit.

The kit of the present invention may provide, for example, a substance A and a substance B by mixing them in the same container, or it may provide them in separate containers. "Written instructions" may be written or printed on paper or another medium, or may be recorded in an electronic medium such as a magnetic tape, a computer-readable disk or tape, or a CD-ROM. In addition, the kit of the present invention may be provided with a container that contains a diluent, a solvent, a washing liquid, or another reagent.

<Antibody>

There are no particular limitations on the antibody of the present invention, provided that it is an antibody that specifically binds with the protein of the present invention. It is acceptable to use a polyclonal antibody against the aforementioned protein, but use of a monoclonal antibody against the aforementioned protein is preferable. A monoclonal antibody is superior from the standpoint that it has advantages such as that its properties are uniform, its supply is easy, and its producing cells can be semi-permanently preserved as hybridoma.

As the antibody of the present invention, one may cite immunoglobulin (IgA, IgD, IgE, IgG, IgM, and the Fab fragment, F(ab')$_2$ fragment, or Fc fragment thereof). Specifically, one may cite a polyclonal antibody, a monoclonal antibody, a single-chain antibody, and an anti-idiotypic antibody, but one is not limited thereto.

The antibody of the present invention may be produced according to various known methods. For example, a monoclonal antibody can be produced by using conventional techniques known in this field (see, e.g., the hybridoma technique (Kohler, G. and Milstein C., Nature 256, 495-497 (1975)), the trioma technique, the human B-cell hybridoma technique (Kozbor, Immunology Today 4, 72 (1983)), and the EBV hybridoma technique (Monoclonal Antibodies and Cancer Therapy, Alan R. Liss, Inc., 77-96 (1985)), etc.).

A peptide antibody can also be produced according to conventional methods known in this field (e.g., Chow, M., et. al., Proc. Natl. Acad. Sci. USA (1985) vol. 82, pp. 910-914; Bittle, F. J. et. al., J. Gen. Virol. (1985) vol. 66, pp. 2347-2354).

As stated above, the antibody of the present invention includes fragments such as the Fab fragment and the F(ab')$_2$ fragment. Such fragments can be produced by proteolyzing the antibody using a typical enzyme such as papain (produces a Fab fragment) or pepsin (produces a F(ab')$_2$ fragment).

Or such fragments can be produced by application of recombinant DNA technology, or by chemical synthesis.

Breeding Method

First Embodiment

The method of the present embodiment for breeding a plant with improved iron deficiency tolerance and iron and zinc accumulation includes a step for detecting the protein of the present invention contained in an extract from the plant.

In order to discriminate whether or not expression of the protein of the present invention is suppressed in a plant body, the method of the present embodiment for breeding a plant with improved iron deficiency tolerance and iron and zinc accumulation may include a step for detecting the protein of the present invention. Based on the presence or absence of expression of the protein of the present invention, screening is conducted for plants that have iron deficiency tolerance, and iron and zinc accumulation in an edible part thereof.

As stated above, the protein of the present invention suppresses expression of the genes that have important functions when a plant acquires iron from soil. Therefore, a plant in which expression of the aforementioned protein is suppressed exhibits an enhanced ability to acquire iron, as well as improved iron deficiency tolerance, and iron and zinc accumulation.

The plant body bred according to the method of the present embodiment may be a natural plant body, or it may be a transformant.

Extract from the plant may be obtained by the freeze-fracture technique using liquid nitrogen, or by a commercial extraction kit, but one is not limited thereto. "Extract" may be a partially purified substance, or a purified preparation that has passed through several purification steps.

In the breeding method of the present embodiment, as a step in which the protein of the present invention contained in an extract from the aforementioned plant is detected, one may cite a step in which the protein of the present invention is detected by causing the extract from the plant to react with the antibody of the present invention. As stated above, as the aforementioned antibody specifically binds with the protein of the present invention to form an immune complex, it is possible to easily detect the aforementioned protein that is expressed in the plant body by detecting formation of the complex.

Formation of the aforementioned complex is detected, for example, using a method that labels the aforementioned antibody with an isotope or the like in advance, or a method that employs a secondary antibody against the aforementioned antibody. Specifically, one may use the conventional Western blot technique, protein chip technique, or the like.

The antibody of the present invention is also used to good effect in the method of the present embodiment for breeding a plant that has improved iron deficiency tolerance, and enhanced iron and zinc accumulation in an edible part thereof. Therefore, a composition including the antibody of the present invention, or a kit provided with the aforementioned antibody can be used to good effect for breeding a plant that has improved iron deficiency tolerance, and enhanced iron and zinc accumulation in an edible part thereof.

Second Embodiment

The plant breeding method of the present embodiment includes a step for detecting the gene of the present invention contained in an extract from a plant.

With respect to the step for detecting the gene of the present invention contained in an extract from the aforementioned plant, it is preferable to include a step in which an oligonucleotide including a fragment of the gene of the present invention or a complementary sequence thereof is incubated with an extract from the aforementioned plant, and it is more preferable to include a step in which an extract from the plant is hybridized with genomic DNA, mRNA, or cDNA pertaining to mRNA that is derived from the target plant.

By detecting a target gene that is hybridized using the breeding method of the present embodiment, it is possible to easily detect a plant body in which expression of the gene of the present invention is suppressed.

Furthermore, as stated above, the protein of the present invention has an important function in the response of a plant body to iron deficiency. Consequently, minor mutations in the amino acid sequence of the aforementioned protein can affect the iron deficiency tolerance of a plant, and iron and zinc accumulation in an edible part thereof. As it is possible to detect mutation in a single base unit of a gene by using well-known and conventionally used art such as the PCR method, the hybridization method, or the microarray method, these techniques can detect minor mutations in the amino acid sequence of the protein encoded by the aforementioned gene.

Accordingly, by using the plant breeding method of the present embodiment, it is also possible to breed a plant that has improved iron deficiency tolerance and enhanced iron and zinc accumulation in an edible part thereof based on a minor mutation in the amino acid sequence of the aforementioned protein that affects the iron deficiency tolerance of the plant and the iron and zinc accumulation in an edible part thereof.

In the present embodiment, an oligonucleotide signifies several, or several tens of, or several hundreds of nucleotides that are bonded.

The oligonucleotide used in the breeding method of the present embodiment may be employed as a PCR primer or a hybridization probe for purposes of obtaining the gene of the present invention or a fragment thereof.

With respect to the length of the oligonucleotide used in the present embodiment, 7 bases or more is preferable, 15 bases or more is more preferable, 20 bases or more is still more preferable, and 40 bases or more is most preferable. These oligonucleotides are synthesized, for example, by the 392-type synthesizer of Applied Biosystems Incorporated (ABI, 850 Lincoln Center Dr., Foster City, Calif. 94404) or the like.

By using the oligonucleotide in this manner in the breeding method of the present embodiment as a hybridization probe that detects the gene that encodes the protein of the present invention, or as a primer that serves to amplify the aforementioned gene, a plant body or tissue in which expression of the gene of the present invention is suppressed can be easily detected.

Working Examples

Next, the present invention is described in greater detail with reference to working examples, but the present invention is not limited by the following working examples.

(Identification of Rice-Derived, Novel Iron-Binding Proteins)

The present inventors conducted an analysis of iron deficiency induced gene clusters using microarray (Ogo, Y. et. al., J. Exp. Bot. (2006) vol. 57, pp. 2867-2878). Among these gene clusters, attention was focused on one candidate gene AK068028 (NCBI accession number: SEQ ID NO:4) as an iron sensor. As stated above, this gene includes a region that encodes the putative hemerythrin (also known as HHE) domain (see FIG. 1). The hemerythrin domain is preserved in invertebrates, bacteria, and mammals, and is known to bind with ferrous iron and molecular oxygen.

In invertebrates, proteins having a hemerythrin domain function as oxygen-transport proteins.

Figure 3:
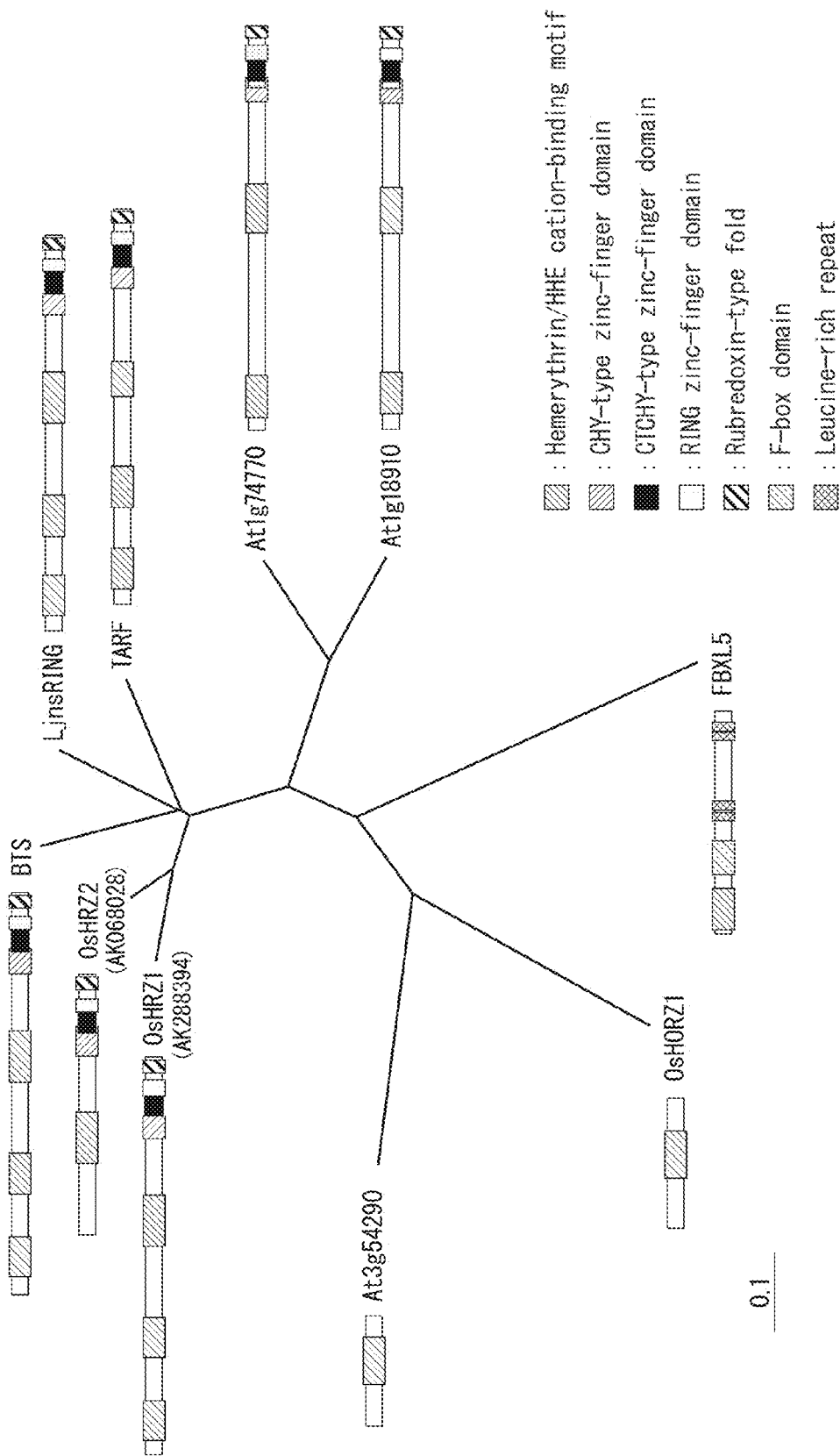
FIG. 3 shows a phylogenetic tree and domain structure of some proteins having hemerythrin domains.

On the other hand, in humans, FBXL5 protein is known as a protein that has a hemerythrin domain (see FIG. 3). It is known that the hemerythrin domain in human FBXL5 protein functions as an iron sensor, and that FBXL recognizes and degrades Iron Regulatory Protein 2 (hereinafter "IRP2") via the F-box domain that functions as a component of E3 ligase of the ubiquitin-proteasome system (Rouault, T. A., Science (2009) vol. 326, pp. 676-677; Vashisht, A., et al., Science (2009) vol. 326, pp. 718-721; Salahudeen, A. A., et al., Science (2009) vol. 326, pp. 722-726).

Most interestingly, the protein that is encoded by the gene represented by SEQ ID NO:4 did not include the F-box domain, but it includes the RING zinc-finger domain that functions as an E3 ligase in a similar manner as the F-box domain (see FIG. 1). The protein that is encoded by the gene represented by SEQ ID NO:4 includes two other zinc-finger domains that are presumed to contribute to transcriptional regulation, post-transcriptional regulation, regulation of protein degradation, and the like, and a Rubredoxin-type motif that is presumed to form iron-sulfur clusters for purposes of electron transfer (see FIG. 1).

As a result of database searches with respect to genes including regions that encode the hemerythrin domain, two more have been discovered in rice (see FIG. 3; OsHORZ1 and the below-mentioned OsHRZ1), and four have been discovered in thale cress (see FIG. 3; BTS, At3g54290, At1g74770, At1g18910). Among these, the protein encoded by AK288394 (NCBI accession number: SEQ ID NO:3) includes the entire domain structure of the protein encoded by the gene represented by SEQ ID NO:4, and includes two more hemerythrin domains (see FIG. 1).

Consequently, the present inventors named the proteins encoded by the genes represented by SEQ ID NO:3 and 4 as *Oryza sativa* Hemerythrin motif-containing Really Interesting New Gene (RING)- and Zinc-finger protein (hereinafter "OsHRZ") 1 and OsHRZ2, respectively.

cDNA fragments of OsHRZ1 and OsHRZ2 were amplified from the cDNA pool of the rice cultivar "Tsukinohikari" using PCR, these amplified products were inserted into a pCR (registered trademark)—Blunt II—TOPO (registered trademark) vector, and the base sequences were confirmed.

(Changes in Expression Level of OsHRZ1 and OsHRZ2 in Response to Iron Deficiency Culture Conditions)

Changes in the expression level of mRNA of OsHRZ1 and OsHRZ2 in leaf and root of the rice cultivar "Nipponbare" were analyzed using quantitative RT-PCR under iron-sufficient conditions and iron-deficient conditions.

In detail, an RNA sample was extracted from rice root or leaf blade obtained by hydroponic culture, treated with DNaseI, and reverse-transcribed using a NucleoSpin RNA Plant Mini Kit (manufactured by Macherey-Nagel) and ReverTra Ace (manufactured by Toyobo Corp.), or an RNeasy Plant Mini Kit (manufactured by Qiagen N.V.) and a ReverTra Ace qRT-PCR RT Master Mix with gDNA Remover (manufactured by Toyobo Corp.). Next, using cDNA synthesized by reverse transcription reaction, real-time PCR was conducted by the StepOnePlus (registered trademark) Real-Time PCR System (manufactured by Applied Biosystems Inc.). As a reagent, SYBR Green I and ExTaq (registered trademark) Real-Time-PCR version (manufactured by TaKaRa Corp.), or TaqMan Gene Expression Assays (manufactured by Applied Biosystems Inc.) were used. The amount of target transcript was normalized using the rice α-2 tubulin transcript level, and represented as the number of copies per total RNA of 1 µg.

The results are shown in FIG. 4. The horizontal axes of the graphs of FIG. 4 show the number of days of culture under iron-sufficient conditions and iron-deficient conditions. +7d represents a rice-derived sample after 7 days of culture under iron-sufficient conditions, −1d represents a rice-derived sample after 1 day of culture under iron-deficient conditions, and −7d represents a rice-derived sample after 7 days of culture under iron-deficient conditions. The vertical axes of the graphs of FIG. 4 represent the number of copies of OsHRZ1 and OsHRZ2 per 1 µg of RNA. FIG. 4(a) represents the expression level in roots, and FIG. 4(b) represents the expression level in leaf blades. The left side of FIG. 4 represents the expression level in OsHRZ1, and the right side of FIG. 4 represents the expression level in OsHRZ2. With respect to significant differences in the following working examples, statistical analyses were conducted using t-test. In the following drawings, * indicates $P<0.05$, and ** indicates $P<0.01$.

As shown in FIG. 4, with respect to both leaf and root, increases in the mRNA expression level of OsHRZ1 and OsHRZ2 under iron-deficient conditions were confirmed.

(Evaluation of Iron-Binding Capability of Recombinant OsHRZ1 Protein and OsHRZ2 Protein)

It was not known whether a plant-derived hemerythrin domain has the ability to bind with iron. The present inventors first prepared expression vectors in which the gene that encodes maltose binding protein (MBP) having full-length HRZ gene or an HRZ-deleted mutant gene on the downstream thereof is inserted into pMAL-c2 (prepared by New England Biolabs).

Next, multiple deletion mutants of these maltose binding protein (MBP)-fused OsHRZ recombinant proteins were prepared by causing expression in *Escherichia coli* BL21 (DE3) pLysS. An MBP fusion system (manufactured by New England Biolabs) was used for expression and purification of recombinant proteins. The manual was followed, except that the *Escherichia coli* was incubated at 22° C.-25° C., and EDTA was removed from the column buffer. After the recombinant proteins were subjected to SDS-PAGE and separated, the purity of the recombinant proteins was confirmed by Coomassie brilliant blue dye. After the expressed recombinant proteins were desalted using PD-10 columns (manufactured by GE Healthcare), purification was conducted using anion-exchange columns (Q-Sepharose, manufactured by GE Healthcare). The domain structure of the prepared recombinant proteins is shown in FIG. 5.

Figure 5:
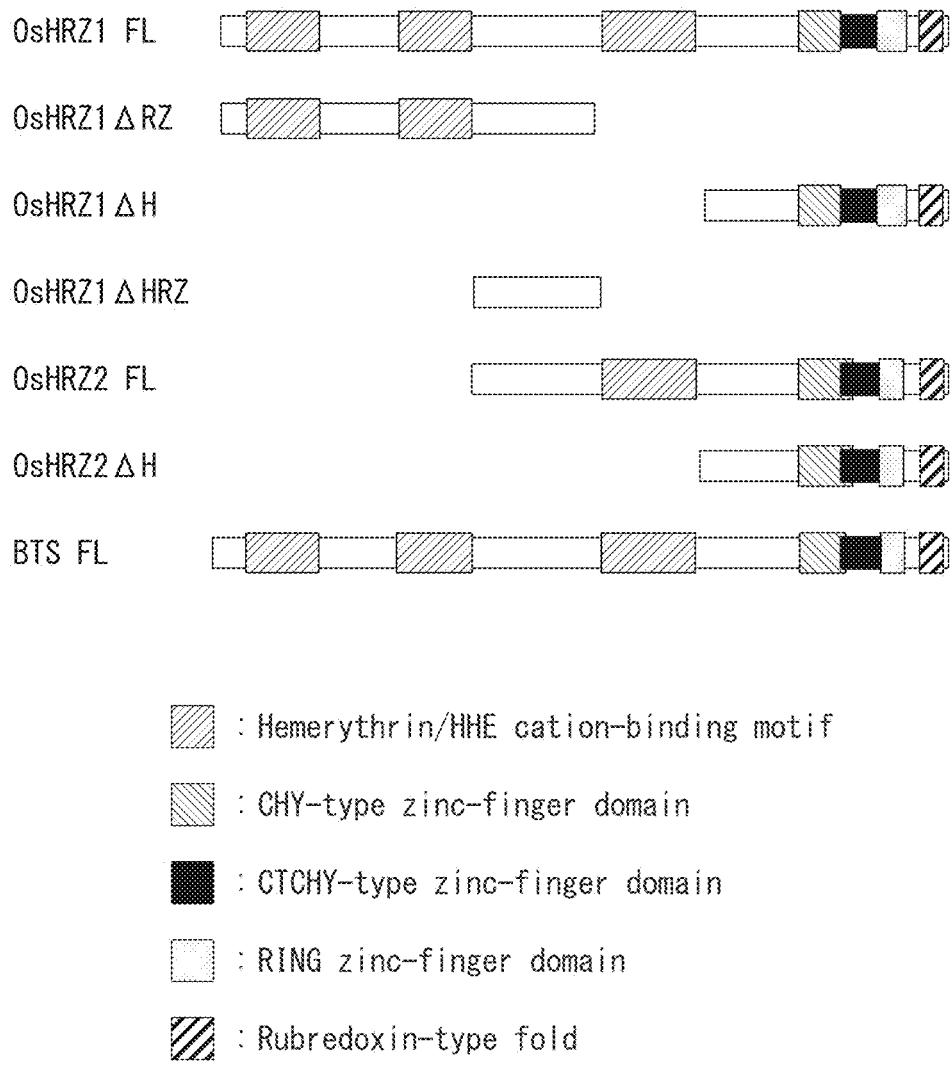
FIG. 5 illustrates domain structures of constructed recombinant proteins.

In FIG. 5, OsHRZ1 FL represents the full-length OsHRZ1 protein, and OsHRZ1 ΔRZ represents a protein with deletion of the C-terminal domains—including the third hemerythrin domain located on the C-terminal side, the three zinc-finger domains that are presumed to contribute to transcriptional regulation, post-transcriptional regulation, regulation of protein degradation, and the like, and the Rubredoxin-type motif that is presumed to form iron-sulfur clusters for electron transfer—from the full-length OsHRZ1 protein. OsHRZ1 ΔH represents a protein with deletion of the N-terminal domains—including the entirety of the three hemerythrin domains—from the full-length OsHRZ1 protein. OsHRZ1 ΔHRZ represents a protein with deletion of N-terminal domains including the entirety of the two hemerythrin domains as located on the N-terminal side, and the C-terminal domains including the third hemerythrin domain located on the C-terminal side, the three zinc-finger domains, and the Rubredoxin-type motif—from the full-length OsHRZ1 protein.

In FIG. 5, OsHRZ2 FL represents the full-length OsHRZ2 protein, and OsHRZ1 AH represents a protein with deletion of the N-terminal domains including the hemerythrin domain from the full-length OsHRZ2 protein. BTS FL represents the full-length protein of the thale cress homologue of OsHRZ1 and OsHRZ2 (see FIG. 3).

The concentrations of metal bound to these proteins were measured by inductively coupled emission spectrometry. Specifically, the purified protein was quantified using a Bio-Rad Protein Assay Kit (manufactured by Bio-Rad Corp.), and 0.1-1 mg of a purified protein solution was treated for 20 minutes at 220° C. in 2 mL of 13.4 M $HNO_3$ using a MarsXpress oven (manufactured by CEM Corp.), and underwent wet ashing. The molar concentrations of iron and zinc were measured using an inductively coupled plasma atomic emission spectrometry (ICPS-8100, manufactured by Shimadzu Corp.). The results are shown in FIG. 6.

Figure 6:
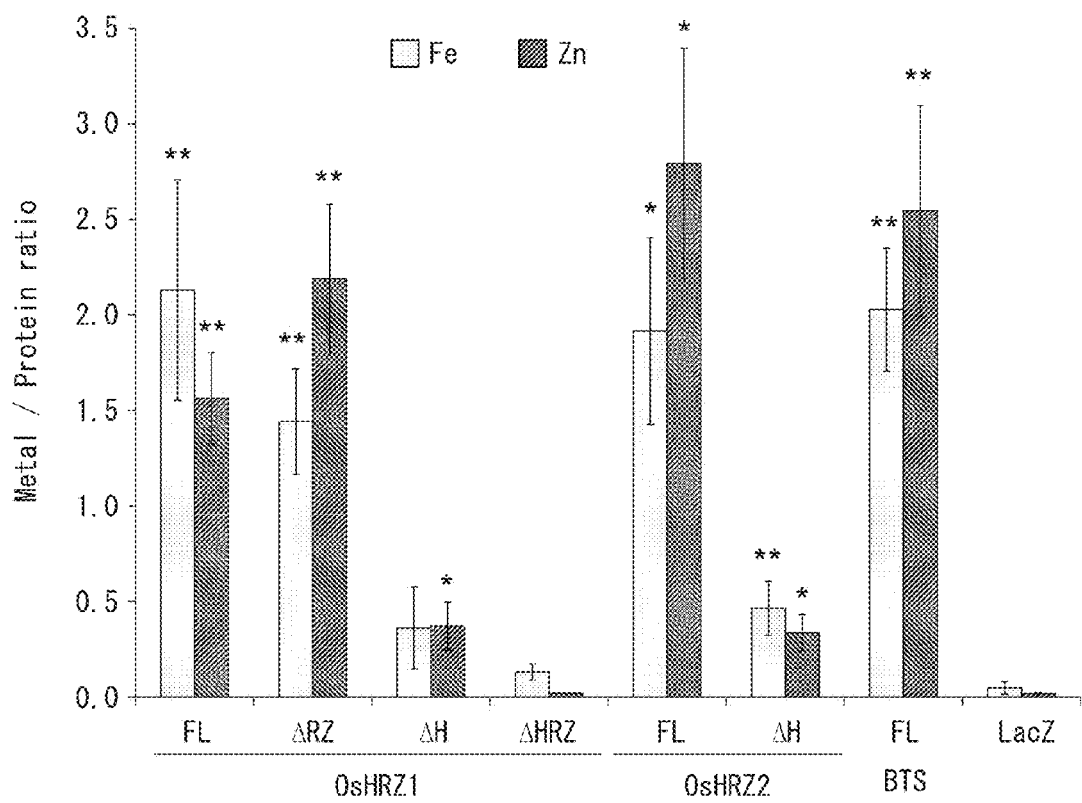
FIG. 6 illustrates analytic results concerning the metal-binding capability of wild-type and mutant-type OsHRZ proteins.

In FIG. 6, the horizontal axis of the graph illustrates the type of recombinant proteins that were employed, and the vertical axis of the graph illustrates the molar number of the iron or zinc bound to 1 mol of protein. As shown in FIG. 6, the full-length OsHRZ1 protein and the full-length OsHRZ2 protein contain iron and zinc in a molar amount that is approximately 2-fold, and this binding ability is decreased to approximately 0.5-fold mol or less by deleting the hemerythrin domains. On the other hand, even when the three zinc-finger domains and the Rubredoxin-type motif were deleted, there was no conspicuous decrease in the iron and zinc binding amount per 1 mol of protein.

Figure 7:
FIG. 7 shows a photograph of tubes containing respective recombinant protein solutions.

As shown in FIG. 7, this is also evident from the iron-derived red-brownish color that is exhibited more by the condensed solution of OsHRZ1 FL protein including the hemerythrin domains than by the condensed solution of OsHRZ1 ΔH protein that does not include the hemerythrin domains.

From this, it was confirmed with respect to the OsHRZ proteins that iron and zinc bind mainly to the hemerythrin domains, rather than to the zinc-finger domains or the Rubredoxin-type motif. Moreover, as thale cress BTS protein also exhibits binding with iron and zinc in a similar manner as OsHRZ1 protein and OsHRZ2 protein, it was found that hemerythrin-type iron- and zinc-binding protein is conserved across plant species.

(Confirmation of Iron Deficiency Tolerance in Rice in which Expression of the OsHRZ Gene is Suppressed)

To investigate the functions of OsHRZ, transformed rice was prepared in which expression of OsHRZ was suppressed by the RNAi technique. Specifically, a fragment of 335 bp (the base sequence represented by SEQ ID NO:5) corresponding to the full length of 3'UTR of OsHRZ2 and a part of the coding region was amplified, and this amplified product was inserted into pENTR (registered trademark)-Blunt II-TOPO (registered trademark) vector. Next, by means of LR clonase reaction, this fragment was introduced one copy in each of the forward and reverse directions separated by a linker sequence into a destination vector pIG121-RNAi-DEST (Ogo, Y. et al., Plant J. (2007) vol. 51, pp. 366-377) to prepare an expression vector.

Next, according to established methods, three transformants (2i-1 to 2i-3) in which expression of OsHRZ2 was suppressed were constructed (Hiei, Y. et. al., Plant J. (1994) vol. 6, pp. 271-282; Kobayashi, T. et. al., Planta (2001) vol. 212, pp. 864-871).

The constructed transformants were cultivated for 7 days under iron-deficient conditions, and the mRNA expression level of OsHRZ2 was analyzed in each transformant using the aforementioned quantitative RT-PCR technique.

Figure 8:
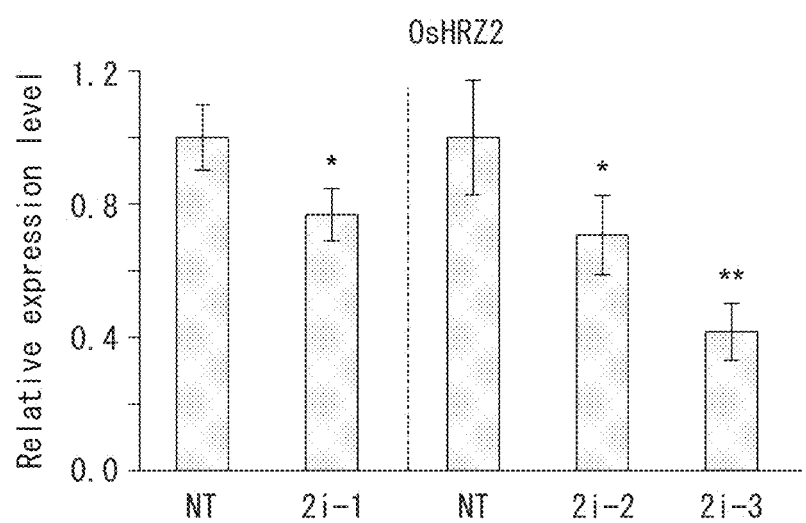
FIG. 8 illustrates analytic results concerning expression levels of mRNA of OsHRZ2 obtained using quantitative RT-PCR with respect to OsHRZ2 expression-suppressing strains.

As shown in FIG. 8, suppression of OsHRZ2 expression was confirmed in these transformants. Furthermore, under normal cultivation conditions, it was confirmed that these transformants grow healthily without exhibiting any remarkable phenotypes.

Figure 9:
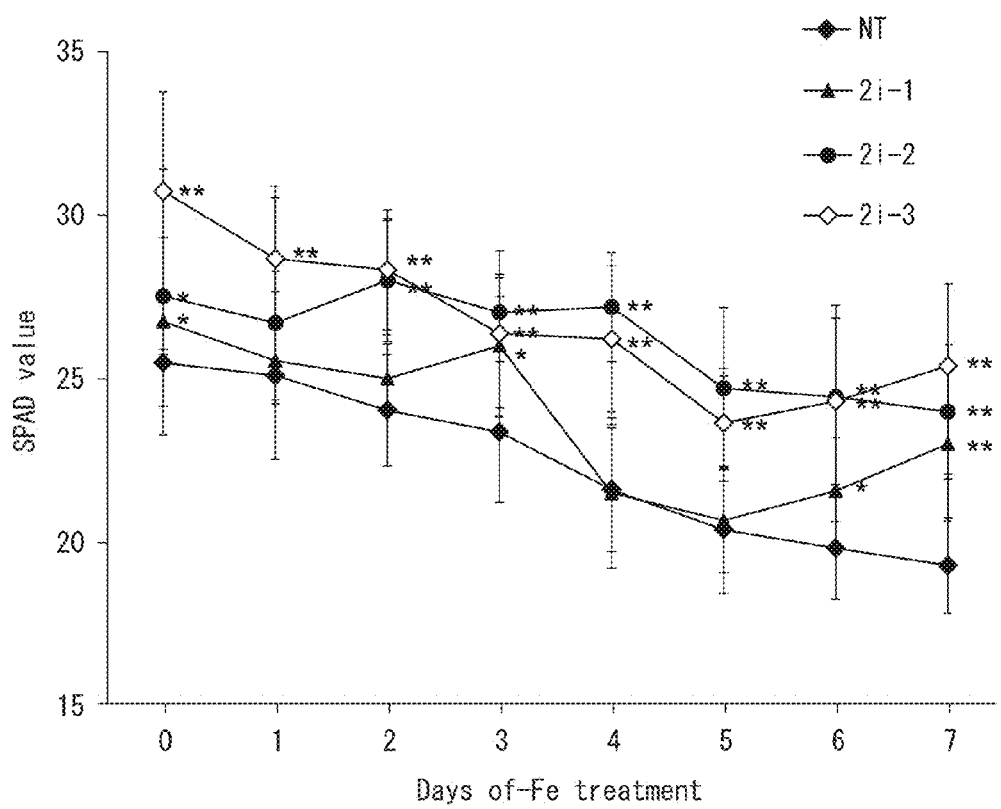
FIG. 9 illustrates quantitative results of chlorophyll content in the newest leaves of OsHRZ2 expression-suppressed strains under iron-deficient cultivation conditions.

In order to study the effects of iron-deficient cultivation conditions on these transformants, chlorophyll content was quantitated in their newest leaves under iron-deficient cultivation conditions. The results are shown in FIG. 9. In FIG. 9, the vertical axis illustrates chlorophyll content (SPAD value) in the newest leaves, and the horizontal axis illustrates the number of days of cultivation under iron-deficient cultivation conditions. As shown in FIG. 9, the leaves of the OsHRZ2-expression suppressed strains exhibited higher chlorophyll content than non-treated (NT) rice leaf even under iron-deficient conditions. From this, it was confirmed that the transformants exhibit tolerance with respect to iron-deficient cultivation conditions.

Figure 10:
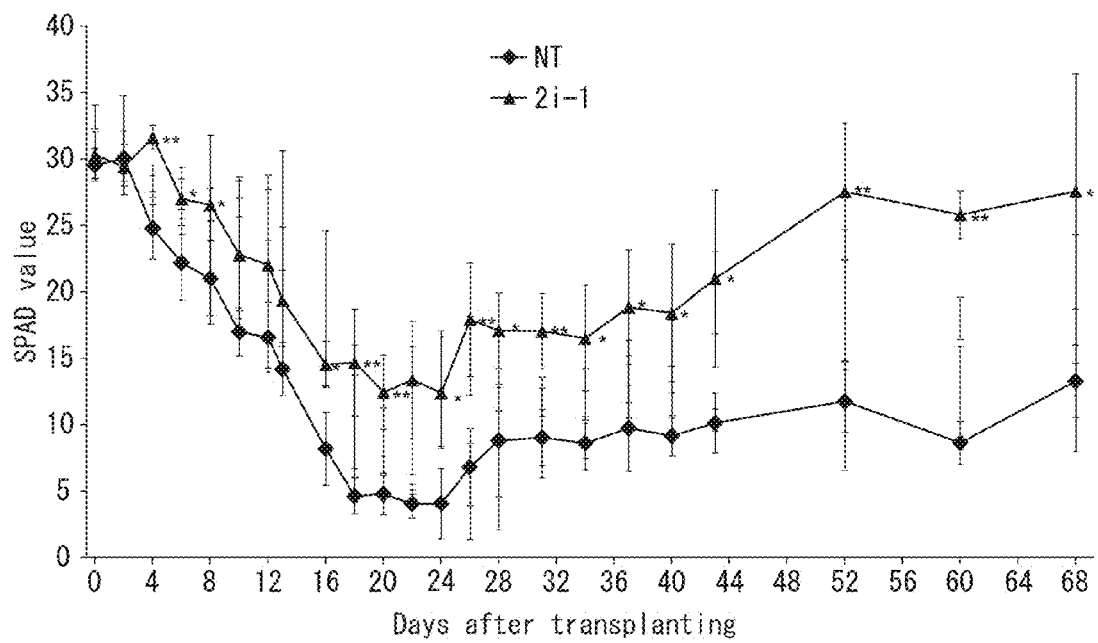
FIG. 10 illustrates quantitative results of chlorophyll content in the newest leaves of an OsHRZ2 expression-suppressed strain under long-term cultivation in calcareous soil.

Furthermore, the present inventors conducted a long-term test of these transformants in calcareous soil with a view to evaluating growth states of these transformants in special soil with little effective iron content. The results are shown in FIG. 10. In FIG. 10, the vertical axis illustrates chlorophyll content (SPAD value) in the newest leaves, and the horizontal axis illustrates the number of days of cultivation after transplantation.

Figure 11:
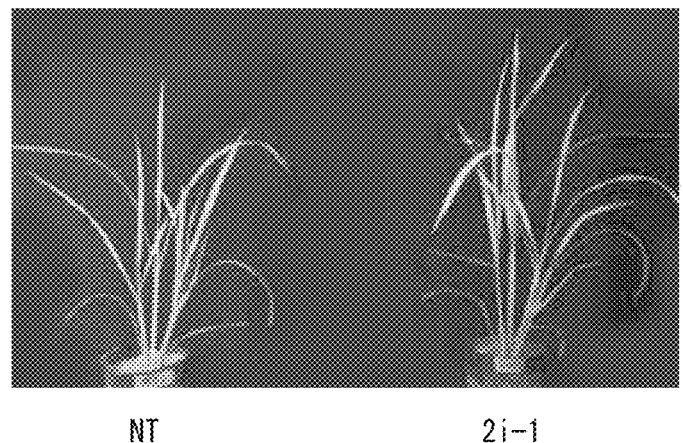
FIG. 11 shows a photograph of shoots of non-treated (NT) rice and an OsHRZ2 expression-suppressed strain that were cultivated for 28 days in calcareous soil.

As shown in FIG. 10, within 20 days after transplant, a decrease in chlorophyll content in the leaves was detected in all rice plants. However, it was confirmed that the extent of the decrease was less in the OsHRZ2 expression-suppressed strain than in the non-treated rice. Furthermore, chlorophyll content in the leaf of the OsHRZ2 expression-suppressed strain gradually recovered from 22 days onward after transplant. As shown in FIG. 11, the seedling height of the OsHRZ2 expression-suppressed strain reflects iron deficiency tolerance. At harvest time, it was confirmed that the OsHRZ2 expression-suppressed strain exhibited a higher resource amount of rice straw and a higher yield amount of grain than non-treated rice.

Furthermore, the present inventors obtained and analyzed an OsHRZ1-disrupted strain in which T-DNA was introduced into the genomic gene of rice, and an OsHRZ2-disrupted strain in which Tos17 was introduced therein. The OsHRZ1-disrupted strain was a 3A-06066 strain obtained by POSTECH Korea (Pohang University of Science and Technology). The OsHRZ2-disrupted strain was an ND6059 strain acquired from the Rice Genome Resource Center, Japan. FIG. 2 shows the state of insertion of (hrz1-1, hrz2-1) into the genome in the OsHRZ1-disrupted strain and the OsHRZ2-disrupted strains.

Genomic DNA was extracted from approximately 0.1 cm$^2$ leaf fragments of the OsHRZ1-disrupted strain and the OsHRZ2-disrupted strain using 100 µl of a 10 mM Tris-HCl (pH 8.0)-0.1 mM EDTA solution. The extracted genomic DNA was subjected to PCR using KOD FX NEO (manufactured by Toyobo Corp.). The results are shown in FIG. 12.

Figure 12:
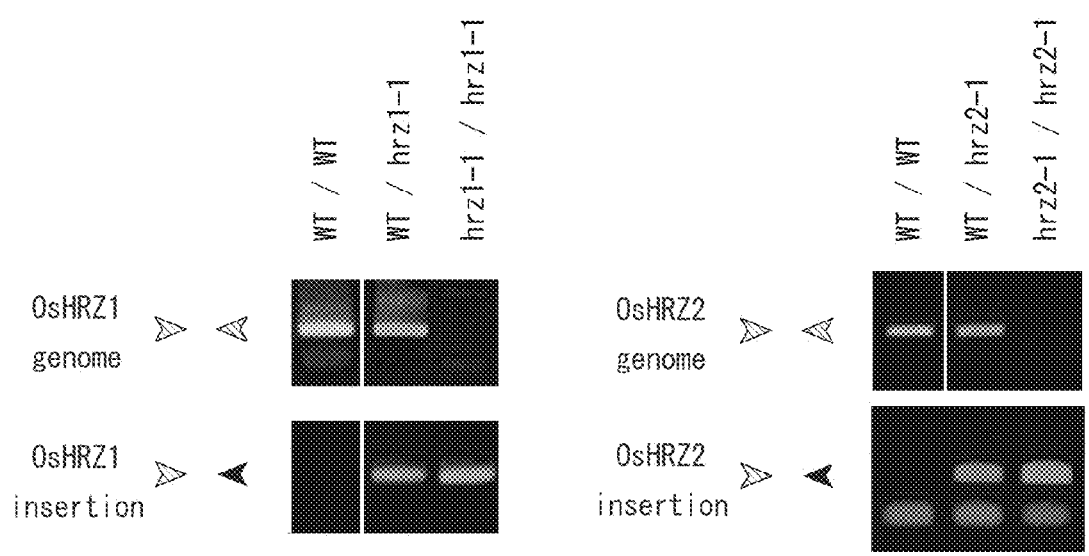
FIG. 12 illustrates results of genomic PCR in OsHRZ-disrupted strains.

In FIG. 12, the arrow marks show the employed primers, and correspond to the primers that were annealed onto the genomic DNA shown in FIG. 2.

As shown in FIG. 12, it was confirmed that hrz1-1 and hrz2-1 experienced a specific insertion of a gene fragment in OsHRZ1 and OsHRZ2, respectively.

Figure 13:
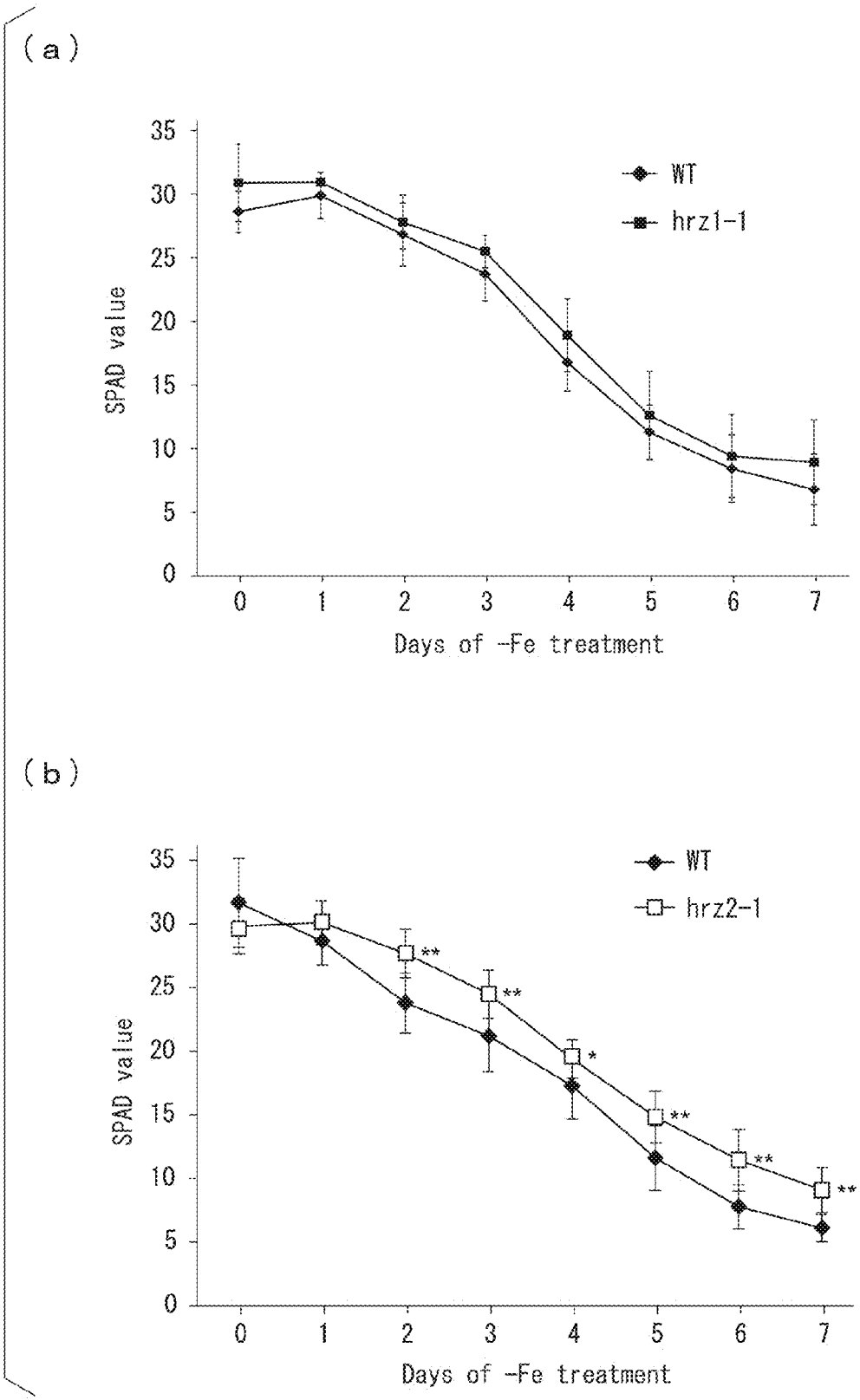
FIG. 13 illustrates quantitative results of chlorophyll content in the newest leaves of OsHRZ-disrupted strains under iron-deficient cultivation conditions.

These disrupted strains were subjected to hydroponic cultivation under iron-deficient conditions, and chlorophyll content in the newest leaves was quantitated. The results are shown in FIG. 13. In FIG. 13, the vertical axes illustrate chlorophyll content (SPAD value) in the newest leaf, and the horizontal axes illustrate the number of days of cultivation under iron-deficient conditions. FIG. 13(a) illustrates chlorophyll content in the newest leaves of non-treated (wild strain: WT) rice and the OsHRZ1-disrupted strain, and FIG. 13(b) illustrates chlorophyll content in the newest leaves of non-treated (wild strain: WT) rice and the OsHRZ2-disrupted strain. As shown in FIG. 13, the OsHRZ1-disrupted strain maintained a slightly higher chlorophyll content than the non-treated rice, and the OsHRZ2-disrupted strain maintained a distinctly higher chlorophyll content than the non-treated rice, confirming that tolerance was exhibited with respect to iron-deficient cultivation conditions.

(Confirmation of Iron Accumulation in Rice Leaf in which Expression of the OsHRZ Gene was Suppressed)

Figure 14:
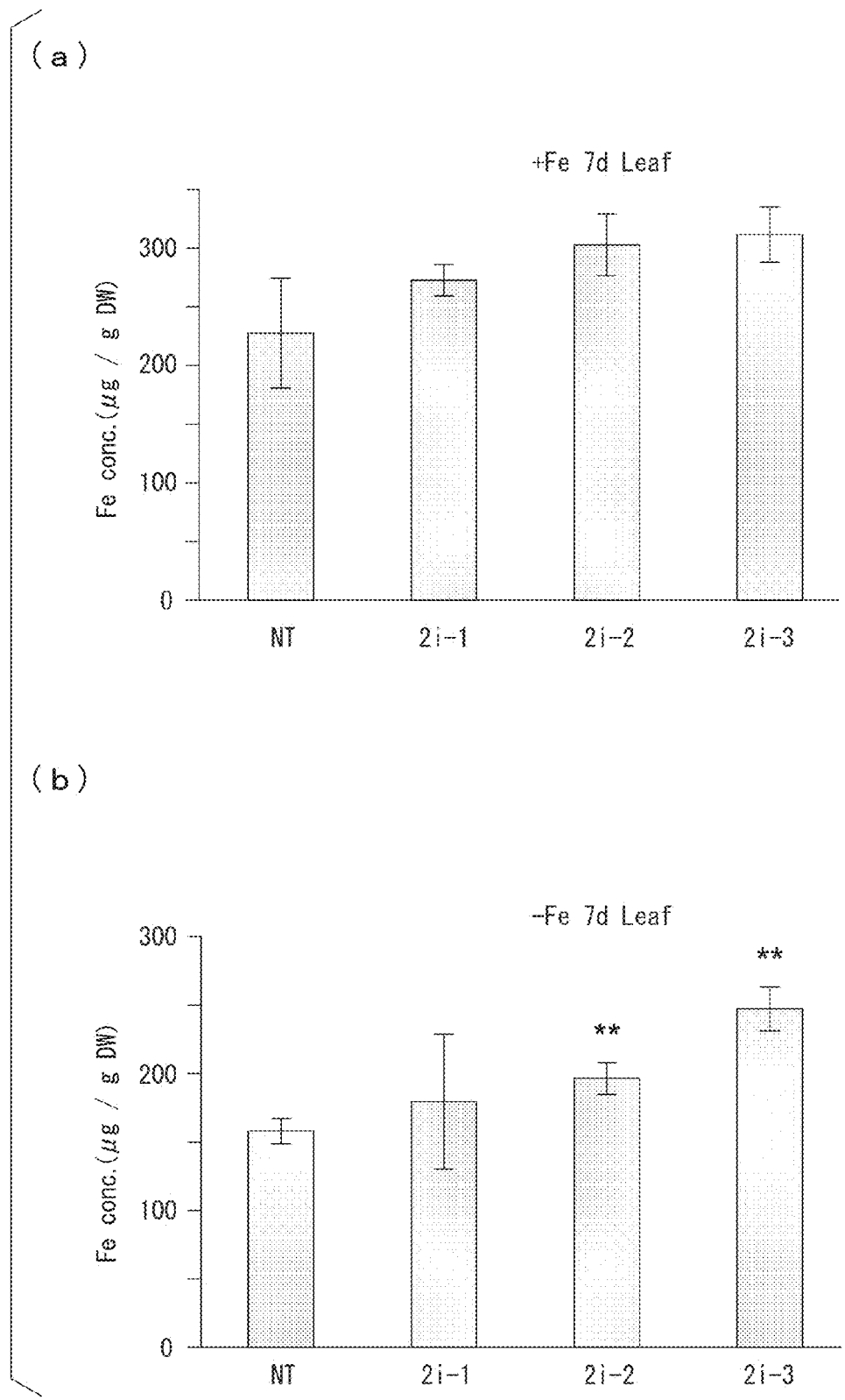
FIG. 14 illustrates accumulated iron concentrations in leaves of OsHRZ2 expression-suppressed strains obtained by hydroponic culture for 7 days under iron-sufficient conditions and iron-deficient conditions.

In order to study the tolerance mechanism of the OsHRZ expression-suppressed strains under iron-deficient cultivation conditions, metal concentrations in leaves of rice subjected to hydroponic cultivation for 7 days were quantitated. The results are shown in FIG. 14. In FIG. 14, the horizontal axes show the types of rice that were used, and the vertical axes show iron concentration in the leaf. As shown in FIG. 14, it was confirmed that, compared to leaves of the non-treated strain, leaves of the OsHRZ2 expression-suppressed strain accumulated higher concentrations of iron under both iron-sufficient conditions (FIG. 14(a)) and iron-deficient conditions (FIG. 14(b)).

(Confirmation of Iron and Zinc Accumulation in Rice Straw and Seed of Rice in which Expression of the OsHRZ Gene was Suppressed)

In order to study iron accumulation in edible parts of rice in which expression of the OsHRZ gene was suppressed, iron concentrations in the rice straw and the seed of rice subjected to pot cultivation were quantitated.

Figure 15:
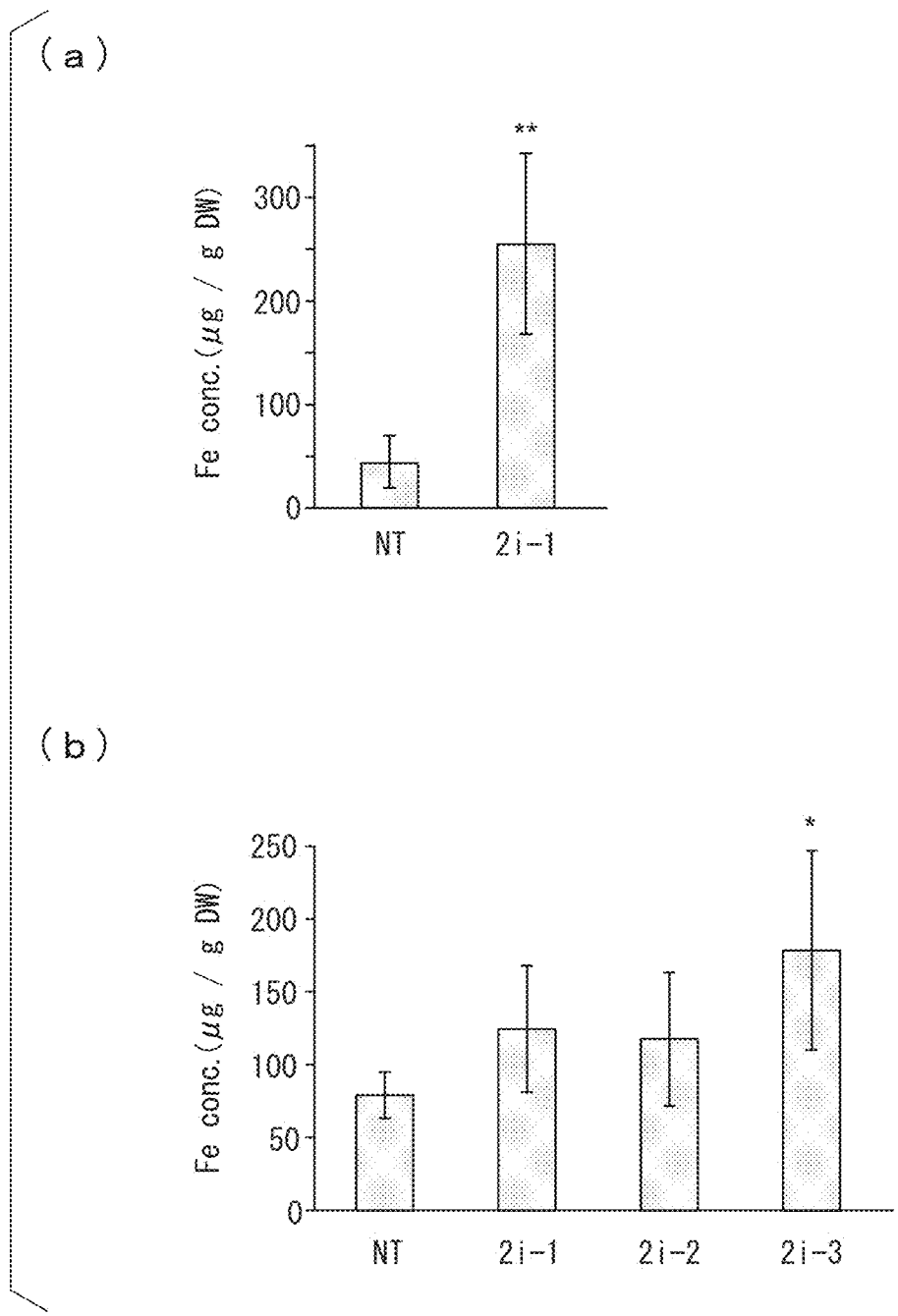
FIG. 15 illustrates accumulated iron concentrations in rice straw of OsHRZ2 expression-suppressed strains obtained by pot cultivation in calcareous soil and normal soil.
Figure 16:
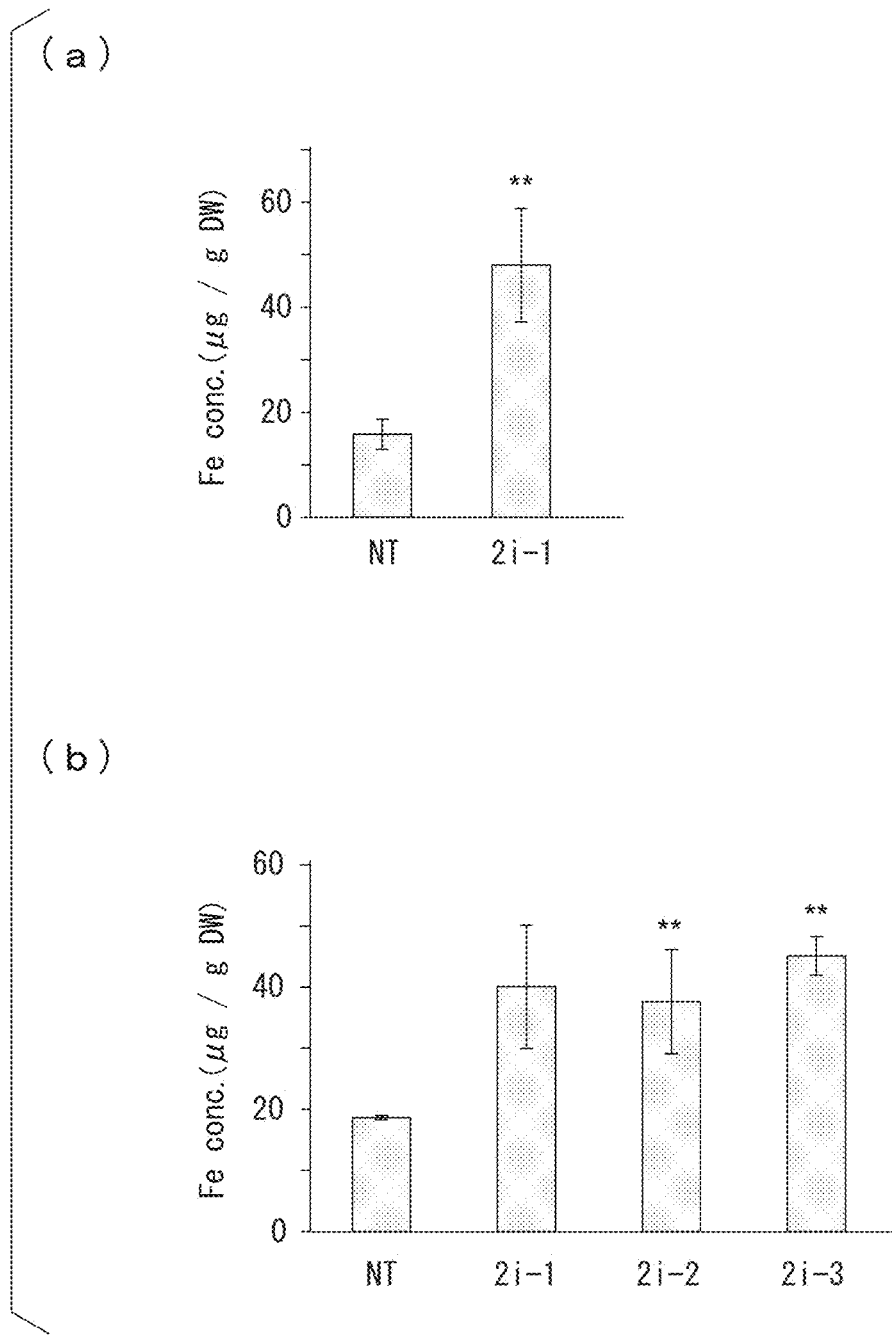
FIG. 16 illustrates accumulated iron concentrations in seeds of OsHRZ2 expression-suppressed strains obtained by pot cultivation in calcareous soil and normal soil.

The results of iron accumulation in rice straw are shown in FIG. 15, and the results of iron accumulation in seed are shown in FIG. 16. In FIG. 15 and FIG. 16, the horizontal axes show the types of rice that were used, and the vertical axes show iron concentration in the rice straw or seed. FIG. 15(a) and FIG. 16(a) show results under iron-deficient conditions when calcareous soil was used, and FIG. 15(b) and FIG. 16(b) show results under iron-sufficient conditions when ordinary soil was used.

As shown in FIG. 15 and FIG. 16, compared to the rice straw and seed of the non-treated strain, it was confirmed that the rice straw and seed of the OsHRZ2 expression-suppressed strain accumulated higher concentrations of iron under both iron-sufficient conditions (FIG. 15(b) and FIG. 16(b)) and iron-deficient conditions (FIG. 15(a) and FIG. 16(a)). From these results, although rice straw is not an edible part, it is considered that the present invention can be adapted to iron enrichment of leafy vegetables and the like.

Similarly, a study was made of iron accumulation in unpolished rice and polished rice cultivated in ordinary soil in an isolation field.

Figure 17:
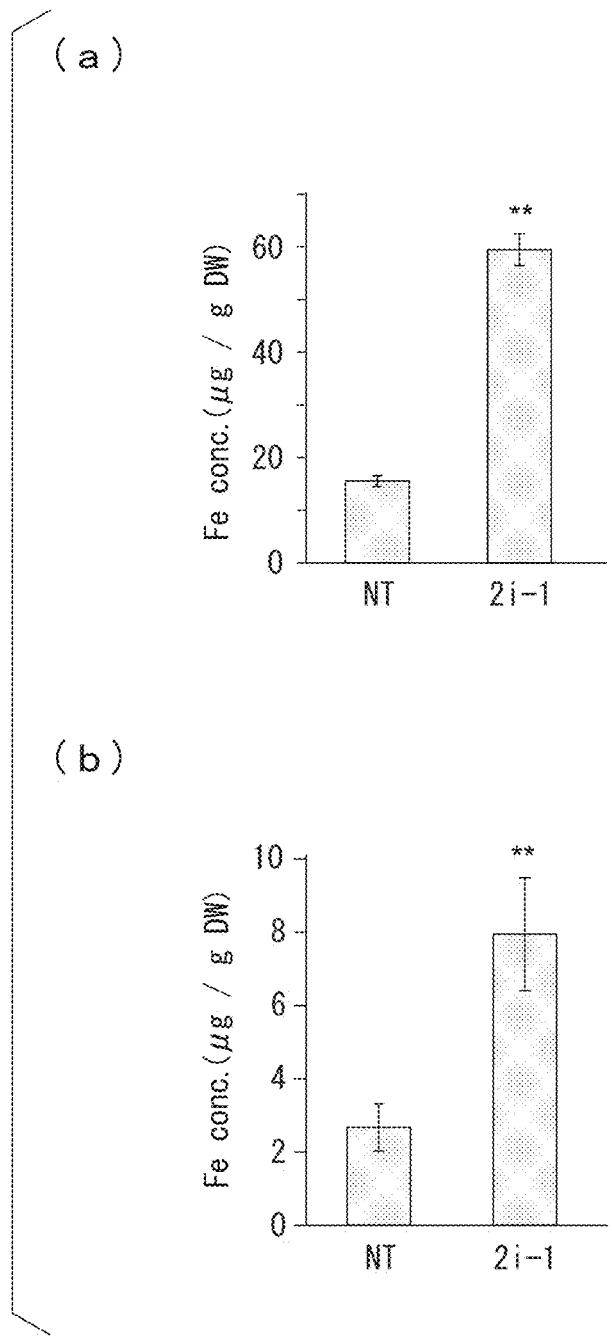
FIG. 17 illustrates accumulated iron concentrations in unpolished rice and polished rice of an OsHRZ2 expression-suppressed strain obtained by cultivation in normal soil in an isolation field.

The results are shown in FIG. 17. FIG. 17(a) shows results for unpolished rice, and FIG. 17(b) shows results for polished rice. In both FIG. 17(a) and FIG. 17(b), the seed of the OsHRZ2 expression-suppressed strain accumulated a higher concentration of iron than the seed of the non-treated strain, thereby confirming that iron is accumulated at a high concentration in an edible part of rice in which expression of the OsHRZ gene is suppressed.

Figure 18:
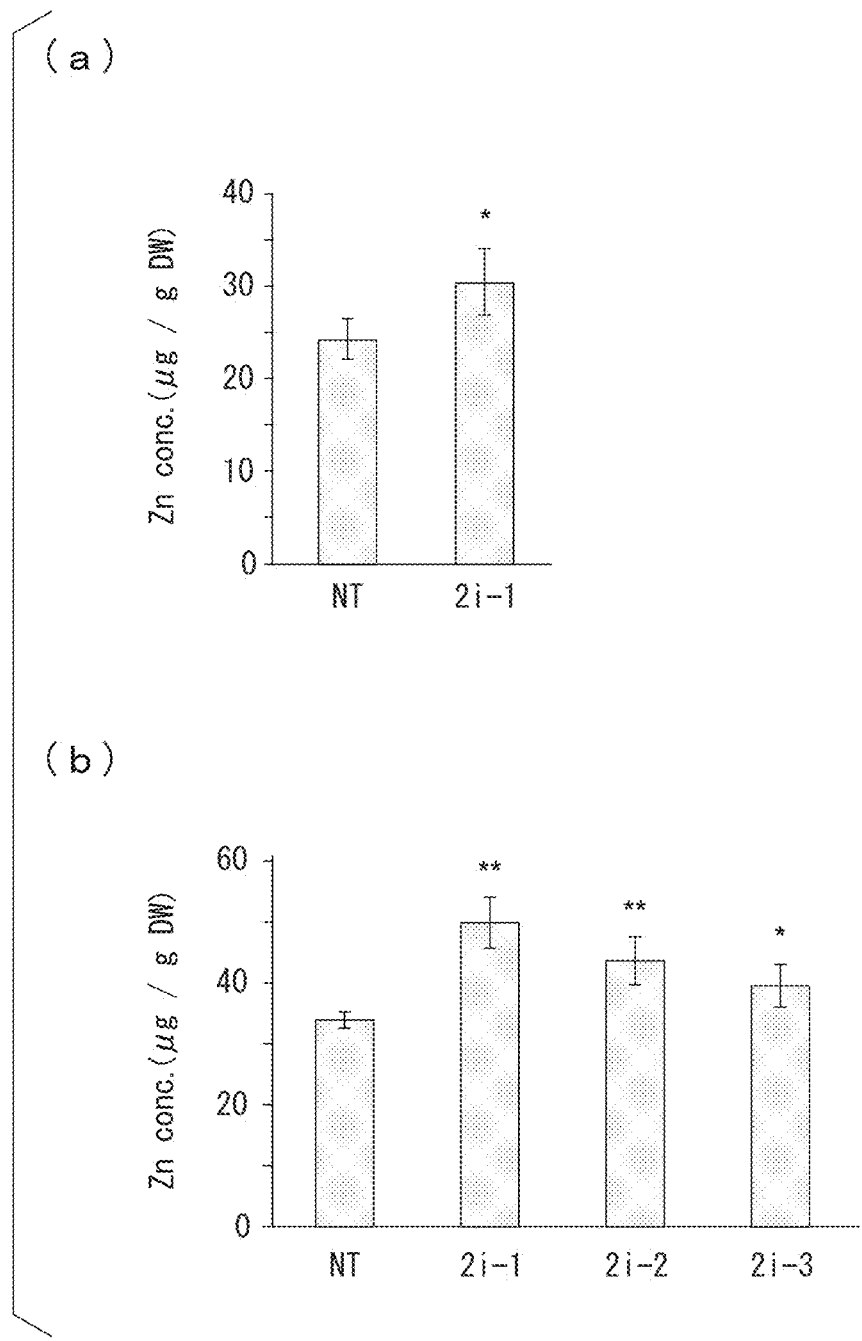
FIG. 18 illustrates accumulated zinc concentrations in seeds of OsHRZ2 expression-suppressed strains obtained by pot cultivation in calcareous soil and normal soil.

In order to study accumulation of zinc in an edible part of rice in which expression of the OsHRZ gene is suppressed, zinc concentration in the seed of rice subjected to pot cultivation was quantitated. FIG. 18(a) shows the results under iron-deficient conditions when calcareous soil was used, and FIG. 18(b) shows the results under iron-sufficient conditions when ordinary soil was used. As shown in FIG. 18, it was confirmed that, compared to the seed of the non-treated strain, the seed of the OsHRZ2 expression-suppressed strain accumulated zinc at a higher concentration under both iron-sufficient conditions and iron-deficient conditions (FIG. 18(a) and FIG. 18(b)).

Figure 19:
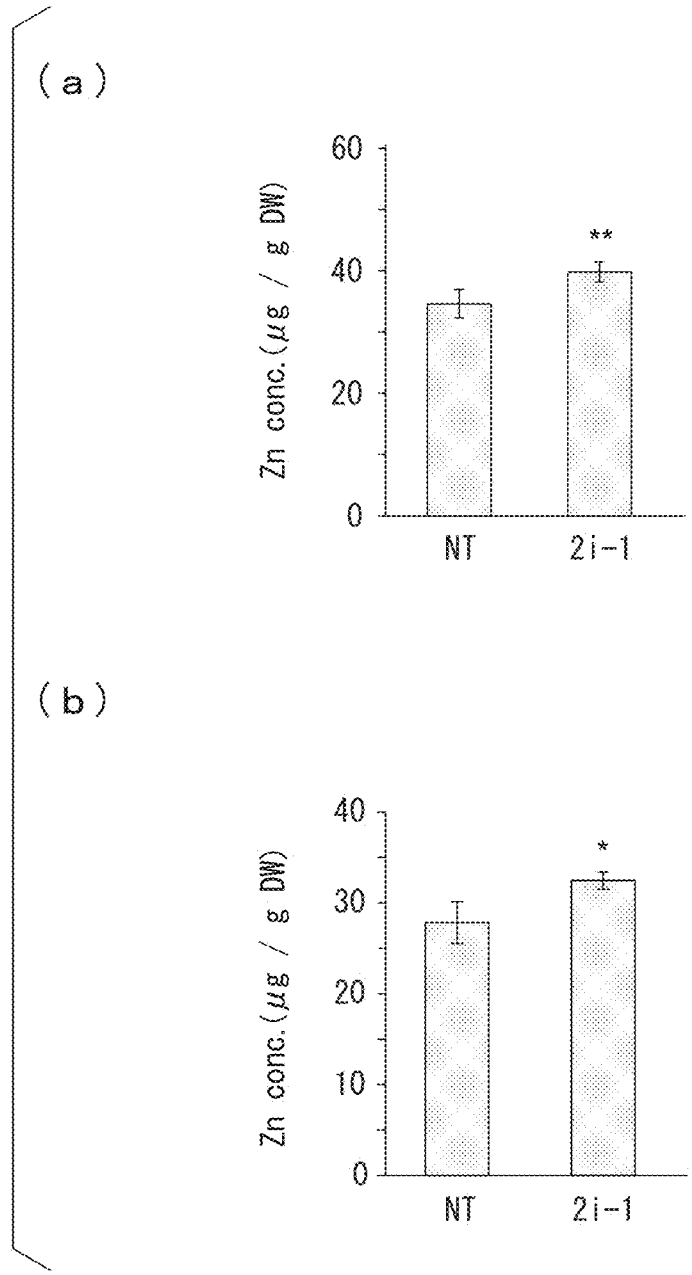
FIG. 19 illustrates accumulated zinc concentrations in unpolished rice and polished rice of an OsHRZ2 expression-suppressed strain obtained by cultivation in normal soil in an isolation field.

With respect to the same rice, a study was made of zinc accumulation in unpolished rice and polished rice cultivated in ordinary soil in an isolation field. The results are shown in FIG. 19. FIG. 19(a) shows the results in unpolished rice, and FIG. 19(b) shows the results in polished rice. In both FIG. 19(a) and FIG. 19(b), the seed of the OsHRZ2 expression-suppressed strain accumulated a higher concentration of zinc than the seed of the non-treated strain, thereby confirming that zinc is accumulated at a high concentration in an edible part of rice in which expression of the OsHRZ gene is suppressed.

Furthermore, a pot test using the same ordinary soil mentioned above was conducted using an OsHRZ1-disrupted strain (hrz1-1) and an OsHRZ2-disrupted strain (hrz2-1). The results are shown in FIG. 20. FIG. 20(a) shows the results of iron accumulation in the seed of the OsHRZ1-disrupted strain (hrz1-1), and FIG. 20(b) shows the results of iron accumulation in the seed of the OsHRZ2-disrupted strain (hrz2-1). In both FIG. 20(a) and FIG. 20(b), the seed of the OsHRZ-disrupted strain accumulated iron in a higher concentration than the seed of the non-treated rice (wild strain: WT). From this, it was confirmed that iron is accumulated in high concentrations in edible parts of OsHRZ-disrupted strains.

A study was also made of zinc accumulation in the seed of OsHRZ-disrupted strains under the same cultivation conditions. The results are shown in FIG. 21. FIG. 21(a) shows the results of zinc accumulation in the seed of the OsHRZ1-disrupted strain (hrz1-1), and FIG. 21(b) shows the results of zinc accumulation in the seed of the OsHRZ2-disrupted strain (hrz2-1). In both FIG. 21(a) and FIG. 21(b), the seed of the OsHRZ-disrupted strain accumulated zinc in a higher concentration than the seed of the non-treated rice (wild strain: WT). From this, it was confirmed that zinc is accumulated in high concentrations in edible parts of OsHRZ-disrupted strains.

Figure 22:
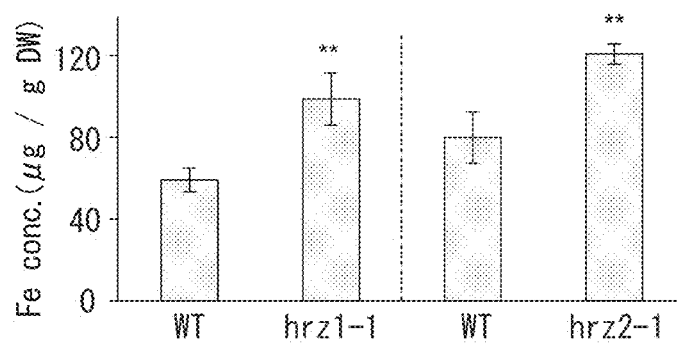
FIG. 22 illustrates accumulated iron concentrations in rice straw of OsHRZ-disrupted strains obtained by pot cultivation in normal soil.
Figure 23:
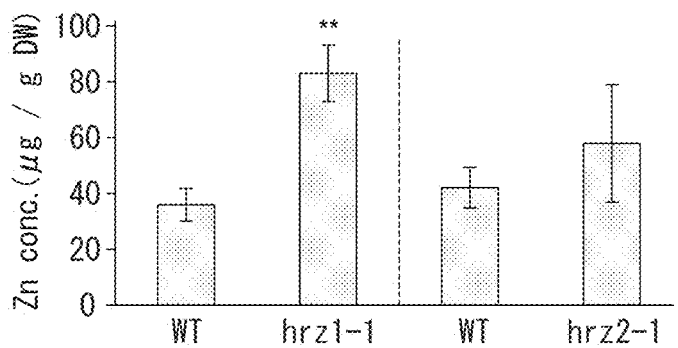
FIG. 23 illustrates accumulated zinc concentrations in rice straw of OsHRZ-disrupted strains obtained by pot cultivation in normal soil.

A study was also made of iron and zinc accumulation in rice straw of OsHRZ-disrupted strains under the same cultivation conditions. FIG. 22 shows the results of iron accumulation in rice straw of OsHRZ-disrupted strains (hrz1-1 and hrz2-1), and FIG. 23 shows the results of zinc accumulation in rice straw of OsHRZ-disrupted strains (hrz1-1 and hrz2-1). In both FIG. 22 and FIG. 23, the rice straw of the OsHRZ-disrupted strains accumulated iron and zinc at higher concentrations than the rice straw of the non-treated rice (wild strain: WT). From this, it was confirmed that iron and zinc accumulate at high concentrations in the rice straw of OsHRZ-disrupted strains.

As the same phenotypes have thus been shown with both transformed rice and OsHRZ-disrupted strains in which expression of OsHRZ is suppressed, it is confirmed that iron and zinc accumulation in the edible parts of rice is improved by suppression of expression of the OsHRZ gene.

(Confirmation of Strengthened Expression of Iron Uptake-Related Genes and Iron Translocation-Related Genes in Rice Roots in which Expression of the OsHRZ Gene is Suppressed)

The present inventors conducted a 44K microarray analysis, and analyzed a genetic expression profile of OsHRZ2 expression-suppressed strains (2i-1 to 2i-3) subjected to hydroponic cultivation under iron-sufficient conditions and iron-deficient conditions. The Rice 44K Microarray (manufactured by Agilent Technologies) includes 60-mer oligonucleotides of 43144 types based on the sequence information obtained from a full-length rice cDNA project. A total RNA was prepared using a NucleoSpin RNA Plant Mini Kit (manufactured by Macherey-Nagel) from roots of OsHRZ2 expression-suppressed strains that were subjected to hydroponic cultivation. Microarray hybridization, data intake, and data analysis were conducted according to previously reported content (Ogo, Y., et. al., J. Exp. Bot. (2006) vol. 57, pp. 2867-2878), and an expression ratio was calculated as (average signal value of the OsHRZ2 expression-suppressed strain)/(average signal value of non-treated (NT) rice). The results are shown in FIG. 24.

FIG. 24 is a drawing which shows expression profiles of the respective genes. As shown in FIG. 24, particularly under iron-sufficient conditions, strengthened expression of various iron uptake-related genes and iron translocation-related genes was exhibited in roots of OsHRZ2 expression-suppressed strains.

Figure 25:
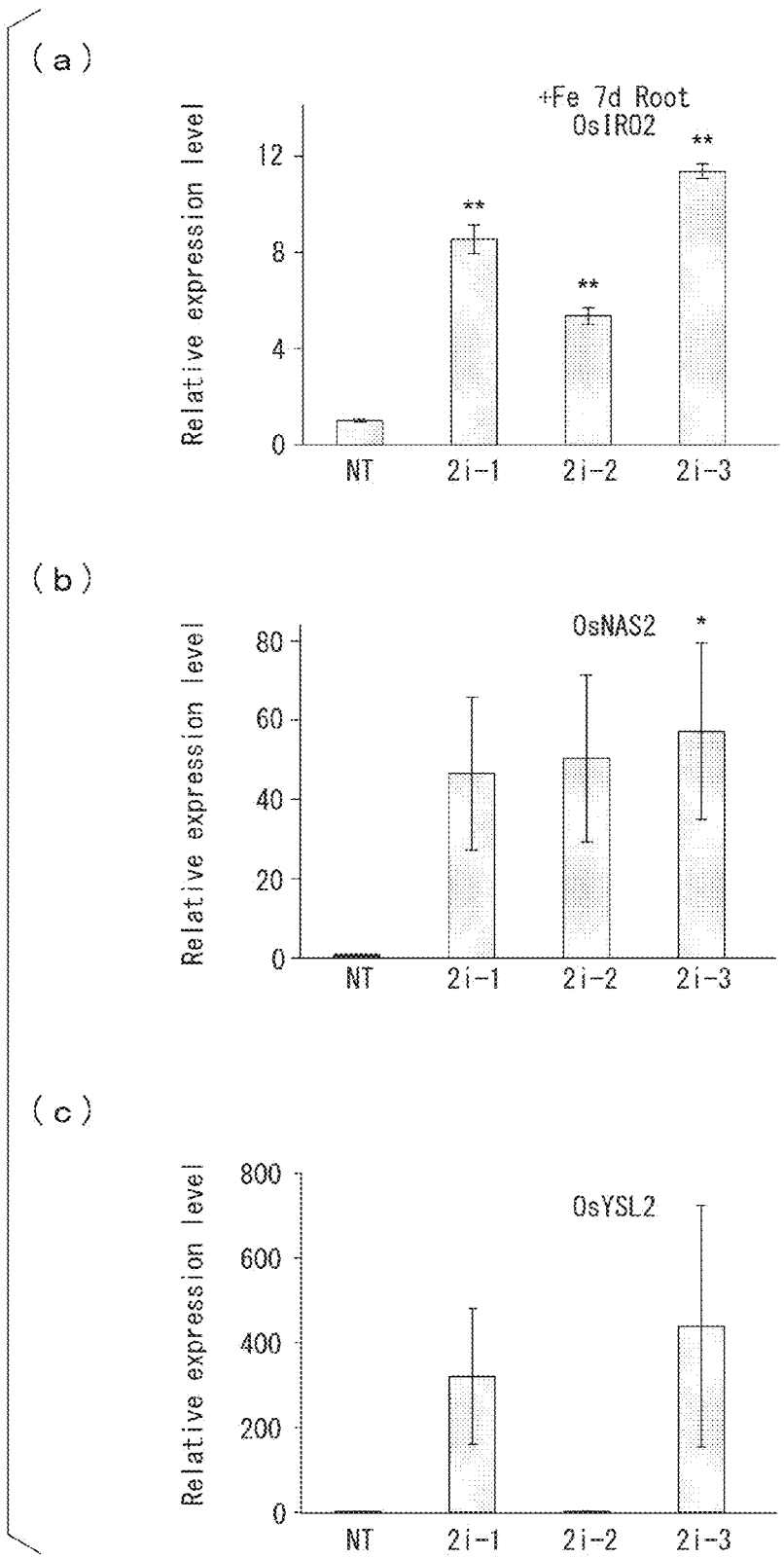
FIG. 25 illustrates results verified using quantitative RT-PCR pertaining to genes for which increased expression was observed in roots of OsHRZ2 expression-suppressed strains under iron-sufficient conditions by microarray analysis.

Furthermore, the results of microarray analysis under iron-sufficient conditions were verified using quantitative RT-PCR. The results are shown in FIG. 25. In FIG. 25, the horizontal axes show the rice strains that were used, and the vertical axes show the expression level of the mRNA of the respective genes (OsIRO2, OsNAS2 and OsYSL2). As shown in FIG. 25, it was confirmed that the change in expression of the respective genes matches the results of microarray analysis.

From this, it was confirmed that OsHRZ proteins are negative regulatory factors that are responsive to iron deficiency, and that it is possible to cancel suppression of expression of iron uptake-related genes and iron translocation-related genes mainly under iron-sufficient conditions by suppressing expression of OsHRZ proteins.

INDUSTRIAL APPLICABILITY

According to the present invention, as it is possible to acquire plants in which iron deficiency tolerance is improved, it is possible to acquire crops that can be grown even in alkaline soil and the like in which there is little solubilized iron content.

Furthermore, according to the present invention, as it is possible to acquire plants in which iron and zinc—and particularly iron—are conspicuously accumulated in edible parts thereof, it is possible to acquire crops that alleviate iron deficiency and zinc deficiency in humans.

In particular, according to the present invention, as it is possible to obtain a trait where the aforementioned iron deficiency tolerance and iron and zinc accumulation in edible parts are simultaneously combined, it is expected to be extremely useful for purposes of stably producing iron-enriched foods under cultivation conditions that have a latent tendency to lapse into iron deficiency such as in semi- and regions or calcareous-prone soil.

Accordingly, the present invention can be suitably used as a "novel iron- and zinc-binding regulatory factors, and technique for improving iron deficiency tolerance of plant and enhancing iron and zinc accumulation in edible part thereof by controlling expression of the novel iron- and zinc-binding regulatory factors," and is extremely useful in industrial terms.

The invention claimed is:

1. A method for breeding a rice plant with improved iron deficiency tolerance and enhanced iron and zinc accumulation in an edible part thereof, the method comprising
   assaying plants to measure an amount of a protein, which is an iron- and zinc-binding regulatory factor, and which comprises any one of the following amino acid sequences of (a) to (c), the protein being contained in extract from the plants, thereby determining a plant with suppressed expression of a gene encoding the protein, and
   breeding the plant with suppressed expression of a gene encoding the protein:
   (a) an amino acid sequence represented by SEQ ID NO:1 or 2;
   (b) an amino acid sequence obtained by deletion, substitution, or addition of one to 10 amino acids in the amino acid sequence represented by SEQ ID NO:1 or 2; or
   (c) an amino acid sequence which has 95% or more identity with the amino acid sequence represented by SEQ ID NO:1 or 2.

2. A method for breeding a plant with improved iron deficiency tolerance, and enhanced iron and zinc accumulation in an edible part thereof, the method comprising
   assaying plants to measure an amount of a polynucleotide corresponding to a gene encoding a protein which is an iron- and zinc-binding regulatory factor and which comprises any one of the following amino acid sequences of (a) to (c), or a polynucleotide corresponding to a gene encoding a protein which is an iron- and zinc-binding regulatory factor, and which comprises any one of the following DNA of (d) to (f), each of the genes being contained in extract from the plants, thereby determining a plant with suppressed expression of the gene, and
   breeding the plant with suppressed expression of the gene:
   (a) an amino acid sequence represented by SEQ ID NO:1 or 2;
   (b) an amino acid sequence obtained by deletion, substitution, or addition of one to 10 amino acids in the amino acid sequence represented by SEQ ID NO:1 or 2;
   (c) an amino acid sequence which has 95% or more identity with the amino acid sequence represented by SEQ ID NO:1 or 2;
   (d) DNA composed of a base sequence represented by SEQ ID NO:3 or 4;
   (e) DNA composed of a base sequence obtained by deletion, substitution, or addition of one to 30 bases in the base sequence represented by SEQ ID NO:3 or 4; or
   (f) DNA composed of a base sequence that has 95% or more identity with the base sequence represented by SEQ ID NO:3 or 4.

3. The method for breeding a plant with improved iron deficiency tolerance and enhanced iron and zinc accumulation in an edible part thereof according to claim 2, wherein each of the plants assayed is obtained using a vector capable of expressing RNAi-inducing nucleic acid suppressing the expression of the gene.

4. The method for breeding a plant with improved iron deficiency tolerance and enhanced iron and zinc accumulation in an edible part thereof according to claim 3, wherein each of the plants assayed is a transformant obtained by introducing the vector into a rice plant host.

* * * * *